US012582421B2

(12) United States Patent
Stemniski et al.

(10) Patent No.: US 12,582,421 B2
(45) Date of Patent: Mar. 24, 2026

(54) INTRAOPERATIVE ADJUSTABLE GUIDES, SYSTEMS, AND METHODS

(71) Applicant: WRIGHT MEDICAL TECHNOLOGY, INC., Memphis, TN (US)

(72) Inventors: Paul M. Stemniski, Memphis, TN (US); Jesse G. Moore, Germantown, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 468 days.

(21) Appl. No.: 18/312,648

(22) Filed: May 5, 2023

(65) Prior Publication Data

US 2023/0363794 A1     Nov. 16, 2023

Related U.S. Application Data

(60) Provisional application No. 63/364,631, filed on May 13, 2022.

(51) Int. Cl.
  *A61B 17/17*          (2006.01)
  *A61B 17/15*          (2006.01)
  *A61B 17/56*          (2006.01)
(52) U.S. Cl.
  CPC .......... *A61B 17/1775* (2016.11); *A61B 17/15* (2013.01); *A61B 17/17* (2013.01); *A61B 17/56* (2013.01); *A61B 2017/568* (2013.01)
(58) Field of Classification Search
  CPC ..... A61B 17/15; A61B 17/17; A61B 17/1775; A61B 2017/565
  See application file for complete search history.

(56) References Cited

U.S. PATENT DOCUMENTS 3,314,420  A      4/1967  Smith et al.
3,605,123  A      9/1971  Hahn
            (Continued)

FOREIGN PATENT DOCUMENTS

AU      2019261830 B2    11/2021
CN         1662186        8/2005
            (Continued)

OTHER PUBLICATIONS

Andersson, et al., "Macintosh Arthroplasty In Rheumatoid Arthritis," Acta. Orthrop. Scand., 1974, pp. 245-259, 45(2).
            (Continued)

*Primary Examiner* — Larry E Waggle, Jr.
(74) *Attorney, Agent, or Firm* — DUANE MORRIS LLP

(57)               ABSTRACT

A system can include a first component having a first body and a second component having a second body. The first body can have a first side and an opposed second side. The first side can have at least one patient-specific surface configured to engage at least one bone in a predetermined manner. The first body can also have a coupling element. The second body can be sized and configured to engage the coupling element to couple the second component to the first component. The second body can include at least one guide surface, and a position of the at least one guide surface can be configured to be adjusted relative to the first component intraoperatively. Methods of using such systems also are disclosed.

13 Claims, 17 Drawing Sheets

(56) References Cited

U.S. PATENT DOCUMENTS

| | | |
|---|---|---|
| 3,798,679 A | 3/1974 | Ewald |
| 3,808,606 A | 5/1974 | Tronzo |
| 3,843,975 A | 10/1974 | Tronzo |
| 3,855,638 A | 12/1974 | Pilliar |
| 3,938,198 A | 2/1976 | Kahn et al. |
| 3,987,499 A | 10/1976 | Scharbach et al. |
| 4,052,753 A | 10/1977 | Dedo |
| 4,055,862 A | 11/1977 | Farling |
| 4,085,466 A | 4/1978 | Goodfellow et al. |
| 4,098,626 A | 7/1978 | Graham et al. |
| 4,203,444 A | 5/1980 | Bonnell et al. |
| 4,213,816 A | 7/1980 | Morris |
| 4,340,978 A | 7/1982 | Buechel et al. |
| 4,368,040 A | 1/1983 | Weissman |
| 4,436,684 A | 3/1984 | White |
| 4,501,266 A | 2/1985 | McDaniel |
| 4,502,161 A | 3/1985 | Wall |
| 4,586,496 A | 5/1986 | Keller |
| 4,594,380 A | 6/1986 | Chapin et al. |
| 4,601,290 A | 7/1986 | Effron et al. |
| 4,609,551 A | 9/1986 | Caplan et al. |
| 4,627,853 A | 12/1986 | Campbell et al. |
| 4,703,751 A | 11/1987 | Pohl |
| 4,704,686 A | 11/1987 | Aldinger |
| 4,715,860 A | 12/1987 | Amstutz et al. |
| 4,721,104 A | 1/1988 | Kaufman et al. |
| 4,759,350 A | 7/1988 | Dunn et al. |
| 4,769,040 A | 9/1988 | Wevers |
| 4,841,975 A | 6/1989 | Woolson |
| 4,846,835 A | 7/1989 | Grande |
| 4,865,607 A | 9/1989 | Witzel et al. |
| 4,880,429 A | 11/1989 | Stone |
| 4,936,862 A | 6/1990 | Walker et al. |
| 4,979,949 A | 12/1990 | Matsen, III et al. |
| 5,002,547 A | 3/1991 | Poggie |
| 5,041,138 A | 8/1991 | Vacanti et al. |
| 5,059,216 A | 10/1991 | Winters |
| 5,067,964 A | 11/1991 | Richmond et al. |
| 5,122,144 A | 6/1992 | Bert et al. |
| 5,129,908 A | 7/1992 | Petersen |
| 5,133,759 A | 7/1992 | Turner |
| 5,154,717 A | 10/1992 | Matsen, III et al. |
| 5,162,430 A | 11/1992 | Rhee et al. |
| 5,171,322 A | 12/1992 | Kenny |
| 5,197,985 A | 3/1993 | Caplan et al. |
| 5,206,023 A | 4/1993 | Hunziker |
| 5,226,914 A | 7/1993 | Caplan et al. |
| 5,234,433 A | 8/1993 | Bert et al. |
| 5,250,050 A | 10/1993 | Poggie et al. |
| 5,258,032 A | 11/1993 | Bertin |
| 5,270,300 A | 12/1993 | Hunziker |
| 5,288,797 A | 2/1994 | Khalil et al. |
| 5,303,148 A | 4/1994 | Mattson et al. |
| 5,306,311 A | 4/1994 | Stone et al. |
| 5,314,482 A | 5/1994 | Goodfellow et al. |
| 5,344,459 A | 9/1994 | Swartz |
| 5,360,446 A | 11/1994 | Kennedy |
| 5,365,996 A | 11/1994 | Crook |
| 5,368,858 A | 11/1994 | Hunziker |
| 5,370,692 A | 12/1994 | Fink et al. |
| 5,380,332 A | 1/1995 | Ferrante |
| 5,387,216 A | 2/1995 | Thornhill et al. |
| 5,454,816 A | 10/1995 | Ashby |
| 5,462,550 A | 10/1995 | Dietz et al. |
| 5,468,787 A | 11/1995 | Braden et al. |
| 5,474,559 A | 12/1995 | Bertin et al. |
| 5,478,739 A | 12/1995 | Slivka et al. |
| 5,486,180 A | 1/1996 | Dietz et al. |
| 5,501,687 A | 3/1996 | Willert et al. |
| 5,503,162 A | 4/1996 | Athanasiou et al. |
| 5,520,695 A | 5/1996 | Luckman |
| 5,523,843 A | 6/1996 | Yamane et al. |
| 5,540,696 A | 7/1996 | Booth, Jr. et al. |
| 5,542,947 A | 8/1996 | Treacy |
| 5,554,190 A | 9/1996 | Draenert |
| 5,556,432 A | 9/1996 | Kubein-Meesenburg et al. |
| 5,571,205 A | 11/1996 | James |
| 5,575,793 A | 11/1996 | Carls et al. |
| 5,578,037 A | 11/1996 | Sanders et al. |
| 5,593,450 A | 1/1997 | Scott et al. |
| 5,597,379 A | 1/1997 | Haines et al. |
| 5,601,563 A | 2/1997 | Burke et al. |
| 5,613,970 A | 3/1997 | Houston et al. |
| 5,616,146 A | 4/1997 | Murray |
| 5,630,820 A | 5/1997 | Todd |
| 5,632,745 A | 5/1997 | Schwartz |
| 5,649,929 A | 7/1997 | Callaway |
| 5,658,290 A | 8/1997 | Techeira |
| 5,671,741 A | 9/1997 | Lang et al. |
| 5,682,886 A | 11/1997 | Delp et al. |
| 5,683,466 A | 11/1997 | Vitale |
| 5,684,562 A | 11/1997 | Fujieda |
| 5,688,282 A | 11/1997 | Baron et al. |
| 5,728,162 A | 3/1998 | Eckhoff |
| 5,735,277 A | 4/1998 | Schuster |
| 5,749,874 A | 5/1998 | Schwartz |
| 5,749,876 A | 5/1998 | Duvillier et al. |
| 5,765,561 A | 6/1998 | Chen et al. |
| 5,768,134 A | 6/1998 | Swaelens et al. |
| 5,769,899 A | 6/1998 | Schwartz et al. |
| 5,786,217 A | 7/1998 | Tuba et al. |
| 5,798,924 A | 8/1998 | Eufinger et al. |
| 5,800,438 A | 9/1998 | Tuke et al. |
| 5,824,083 A | 10/1998 | Draenert |
| 5,827,289 A | 10/1998 | Reiley et al. |
| 5,830,216 A | 11/1998 | Insall et al. |
| 5,835,619 A | 11/1998 | Morimoto et al. |
| 5,842,477 A | 12/1998 | Naughton et al. |
| 5,847,804 A | 12/1998 | Sarver et al. |
| 5,853,746 A | 12/1998 | Hunziker |
| 5,860,981 A | 1/1999 | Bertin et al. |
| 5,871,018 A | 2/1999 | Delp et al. |
| 5,871,542 A | 2/1999 | Goodfellow et al. |
| 5,871,546 A | 2/1999 | Colleran et al. |
| 5,879,390 A | 3/1999 | Kubein-Meesenburg et al. |
| 5,880,976 A | 3/1999 | DiGioia, III et al. |
| 5,885,296 A | 3/1999 | Masini |
| 5,885,297 A | 3/1999 | Matsen, III |
| 5,885,298 A | 3/1999 | Herrington et al. |
| 5,897,559 A | 4/1999 | Masini |
| 5,899,859 A | 5/1999 | Votruba et al. |
| 5,900,245 A | 5/1999 | Sawhney et al. |
| 5,906,934 A | 5/1999 | Grande et al. |
| 5,911,723 A | 6/1999 | Ashby et al. |
| 5,916,220 A | 6/1999 | Masini |
| 5,939,323 A | 8/1999 | Valentini et al. |
| 5,951,475 A | 9/1999 | Gueziec et al. |
| 5,961,523 A | 10/1999 | Masini |
| 5,968,051 A | 10/1999 | Luckman et al. |
| 5,972,385 A | 10/1999 | Liu et al. |
| 5,995,738 A | 11/1999 | DiGioia, III et al. |
| 6,001,895 A | 12/1999 | Harvey et al. |
| 6,002,859 A | 12/1999 | DiGioia, III et al. |
| 6,006,126 A | 12/1999 | Cosman |
| 6,007,537 A | 12/1999 | Burkinshaw et al. |
| 6,010,509 A | 1/2000 | Delgado et al. |
| 6,013,081 A | 1/2000 | Burkinshaw et al. |
| 6,013,103 A | 1/2000 | Kaufman et al. |
| 6,046,379 A | 4/2000 | Stone et al. |
| 6,056,754 A | 5/2000 | Haines et al. |
| 6,056,756 A | 5/2000 | Eng et al. |
| 6,057,927 A | 5/2000 | Levesque et al. |
| 6,077,270 A | 6/2000 | Katz |
| 6,082,364 A | 7/2000 | Balian et al. |
| 6,090,144 A | 7/2000 | Letot et al. |
| 6,093,204 A | 7/2000 | Stone |
| 6,096,043 A | 8/2000 | Techiera et al. |
| 6,102,916 A | 8/2000 | Masini |
| 6,106,529 A | 8/2000 | Techiera |
| 6,110,209 A | 8/2000 | Stone |
| 6,120,541 A | 9/2000 | Johnson |
| 6,126,690 A | 10/2000 | Ateshian et al. |
| 6,139,578 A | 10/2000 | Lee et al. |
| 6,156,069 A | 12/2000 | Amstutz |

(56) References Cited

U.S. PATENT DOCUMENTS

| | | | |
|---|---|---|---|
| 6,161,080 A | 12/2000 | Aouni-Ateshian et al. |
| 6,187,010 B1 | 2/2001 | Masini |
| 6,200,606 B1 | 3/2001 | Peterson et al. |
| 6,203,546 B1 | 3/2001 | MacMahon |
| 6,203,576 B1 | 3/2001 | Afriat et al. |
| 6,205,411 B1 | 3/2001 | DiGioia, III et al. |
| 6,206,927 B1 | 3/2001 | Fell et al. |
| 6,214,369 B1 | 4/2001 | Grande et al. |
| 6,217,894 B1 | 4/2001 | Sawhney et al. |
| 6,219,571 B1 | 4/2001 | Hargreaves et al. |
| 6,224,632 B1 | 5/2001 | Pappas et al. |
| 6,235,060 B1 | 5/2001 | Kubein-Meesenburg et al. |
| 6,251,143 B1 | 6/2001 | Schwartz et al. |
| 6,254,639 B1 | 7/2001 | Peckitt |
| 6,277,151 B1 | 8/2001 | Lee et al. |
| 6,281,195 B1 | 8/2001 | Rueger et al. |
| 6,283,980 B1 | 9/2001 | Vibe-Hansen et al. |
| 6,296,646 B1 | 10/2001 | Williamson |
| 6,299,905 B1 | 10/2001 | Peterson et al. |
| 6,322,588 B1 | 11/2001 | Ogle et al. |
| 6,327,491 B1 | 12/2001 | Franklin et al. |
| 6,328,765 B1 | 12/2001 | Hardwick et al. |
| 6,344,043 B1 | 2/2002 | Pappas |
| 6,344,059 B1 | 2/2002 | Krakovits et al. |
| 6,352,558 B1 | 3/2002 | Spector |
| 6,358,253 B1 | 3/2002 | Torrie et al. |
| 6,365,405 B1 | 4/2002 | Salzmann et al. |
| 6,371,958 B1 | 4/2002 | Overaker |
| 6,373,250 B1 | 4/2002 | Tsoref et al. |
| 6,375,658 B1 | 4/2002 | Hangody et al. |
| 6,379,367 B1 | 4/2002 | Vibe-Hansen et al. |
| 6,382,028 B1 | 5/2002 | Wooh et al. |
| 6,383,228 B1 | 5/2002 | Schmotzer |
| 6,387,131 B1 | 5/2002 | Miehlke et al. |
| 6,429,013 B1 | 8/2002 | Halvorsen et al. |
| 6,443,988 B2 | 9/2002 | Felt et al. |
| 6,443,991 B1 | 9/2002 | Running |
| 6,444,222 B1 | 9/2002 | Asculai et al. |
| 6,459,927 B1 | 10/2002 | Franklin et al. |
| 6,459,948 B1 | 10/2002 | Ateshian et al. |
| 6,468,314 B2 | 10/2002 | Schwartz et al. |
| 6,478,799 B1 | 11/2002 | Williamson |
| 6,479,996 B1 | 11/2002 | Hoogeveen et al. |
| 6,510,334 B1 | 1/2003 | Schuster et al. |
| 6,520,964 B2 | 2/2003 | Tallarida et al. |
| 6,558,421 B1 | 5/2003 | Fell et al. |
| 6,560,476 B1 | 5/2003 | Pelletier et al. |
| 6,575,980 B1 | 6/2003 | Robie et al. |
| 6,620,168 B1 | 9/2003 | Lombardo et al. |
| 6,626,945 B2 | 9/2003 | Simon et al. |
| 6,626,948 B2 | 9/2003 | Storer et al. |
| 6,632,225 B2 | 10/2003 | Sanford et al. |
| 6,632,235 B2 | 10/2003 | Weikel et al. |
| 6,652,587 B2 | 11/2003 | Felt et al. |
| 6,673,077 B1 | 1/2004 | Katz |
| 6,679,917 B2 | 1/2004 | Ek |
| 6,712,856 B1 | 3/2004 | Carignan et al. |
| 6,738,657 B1 | 5/2004 | Franklin et al. |
| 6,905,514 B2 | 6/2005 | Carignan et al. |
| 6,916,341 B2 | 7/2005 | Rolston |
| 6,928,742 B2 | 8/2005 | Broers et al. |
| 6,932,842 B1 | 8/2005 | Litschko et al. |
| 6,942,667 B1 | 9/2005 | Song |
| 6,944,518 B2 | 9/2005 | Roose |
| 6,969,393 B2 | 11/2005 | Pinczewski et al. |
| 6,980,849 B2 | 12/2005 | Sasso |
| 6,988,015 B1 | 1/2006 | Schopf et al. |
| 6,993,374 B2 | 1/2006 | Sasso |
| 7,008,430 B2 | 3/2006 | Dong et al. |
| 7,058,439 B2 | 6/2006 | Eaton et al. |
| 7,060,074 B2 | 6/2006 | Rosa et al. |
| 7,104,997 B2 | 9/2006 | Lionberger et al. |
| 7,115,131 B2 | 10/2006 | Engh et al. |
| 7,117,027 B2 | 10/2006 | Zheng et al. |
| 7,141,053 B2 | 11/2006 | Rosa et al. |
| 7,184,814 B2 | 2/2007 | Lang et al. |
| 7,201,762 B2 | 4/2007 | Green, Jr. et al. |
| 7,217,276 B2 | 5/2007 | Henderson et al. |
| 7,239,908 B1 | 7/2007 | Alexander et al. |
| 7,245,697 B2 | 7/2007 | Lang |
| 7,282,054 B2 | 10/2007 | Steffensmeier et al. |
| 7,292,674 B2 | 11/2007 | Lang |
| 7,347,690 B2 | 3/2008 | Jordan et al. |
| 7,364,581 B2 | 4/2008 | Michalowicz |
| 7,377,924 B2 | 5/2008 | Raistrick et al. |
| 7,379,529 B2 | 5/2008 | Lang |
| 7,467,892 B2 | 12/2008 | Lang et al. |
| 7,468,075 B2 | 12/2008 | Lang et al. |
| 7,534,263 B2 | 5/2009 | Burdulis, Jr. et al. |
| 7,618,451 B2 | 11/2009 | Berez et al. |
| 7,747,305 B2 | 6/2010 | Dean et al. |
| 7,806,896 B1 | 10/2010 | Bonutti |
| 7,881,768 B2 | 2/2011 | Lang et al. |
| 7,981,158 B2 | 7/2011 | Fitz et al. |
| 7,983,777 B2 | 7/2011 | Melton et al. |
| 8,036,729 B2 | 10/2011 | Lang et al. |
| 8,062,302 B2 | 11/2011 | Lang et al. |
| 8,066,708 B2 | 11/2011 | Lang et al. |
| 8,083,745 B2 | 12/2011 | Lang et al. |
| 8,105,330 B2 | 1/2012 | Fitz et al. |
| 8,112,142 B2 | 2/2012 | Alexander et al. |
| 8,122,592 B2 | 2/2012 | Burdulis, Jr. et al. |
| RE43,282 E | 3/2012 | Alexander et al. |
| 8,485,970 B2 * | 7/2013 | Widenhouse .......... A61B 1/018 600/201 |
| 8,496,663 B2 | 7/2013 | White et al. |
| 8,535,319 B2 | 9/2013 | Ball |
| 8,715,362 B2 | 5/2014 | Reiley et al. |
| 8,808,303 B2 | 8/2014 | Stemniski |
| 9,017,334 B2 | 4/2015 | Carroll et al. |
| 9,125,674 B2 | 9/2015 | White et al. |
| 9,265,511 B2 | 2/2016 | White et al. |
| 9,402,640 B2 | 8/2016 | Stemniski et al. |
| 9,480,490 B2 | 11/2016 | Metzger et al. |
| 10,130,430 B2 | 11/2018 | Kao et al. |
| 10,413,308 B2 | 9/2019 | Stemniski et al. |
| 10,653,432 B2 * | 5/2020 | Luttrell ................ A61B 17/151 |
| 10,667,867 B2 | 6/2020 | Ashish et al. |
| 10,835,265 B2 | 11/2020 | White et al. |
| 10,835,266 B2 | 11/2020 | White et al. |
| 11,147,627 B2 | 10/2021 | Gangwar et al. |
| 11,172,945 B1 | 11/2021 | Lian |
| 11,253,275 B2 * | 2/2022 | Abt ........................ A61B 17/15 |
| 2001/0001120 A1 | 5/2001 | Masini |
| 2001/0010023 A1 | 7/2001 | Schwartz et al. |
| 2001/0039455 A1 | 11/2001 | Simon et al. |
| 2002/0013626 A1 | 1/2002 | Geisllich et al. |
| 2002/0029038 A1 | 3/2002 | Haines |
| 2002/0045940 A1 | 4/2002 | Giannelli et al. |
| 2002/0059049 A1 | 5/2002 | Bradbury et al. |
| 2002/0068979 A1 | 6/2002 | Brown et al. |
| 2002/0072821 A1 | 6/2002 | Baker |
| 2002/0079601 A1 | 6/2002 | Russell et al. |
| 2002/0082703 A1 | 6/2002 | Repicci |
| 2002/0087274 A1 | 7/2002 | Alexander et al. |
| 2002/0106625 A1 | 8/2002 | Hung et al. |
| 2002/0115647 A1 | 8/2002 | Halvorsen et al. |
| 2002/0120274 A1 | 8/2002 | Overaker et al. |
| 2002/0120281 A1 | 8/2002 | Overaker |
| 2002/0123817 A1 | 9/2002 | Clasbrummel et al. |
| 2002/0127264 A1 | 9/2002 | Felt et al. |
| 2002/0133230 A1 | 9/2002 | Repicci |
| 2002/0143402 A1 | 10/2002 | Steinberg |
| 2002/0151986 A1 | 10/2002 | Asculai et al. |
| 2002/0156150 A1 | 10/2002 | Asculai et al. |
| 2002/0156479 A1 | 10/2002 | Schulzki et al. |
| 2002/0173852 A1 | 11/2002 | Felt et al. |
| 2002/0183850 A1 | 12/2002 | Felt et al. |
| 2002/0198531 A1 | 12/2002 | Millard et al. |
| 2003/0028196 A1 | 2/2003 | Bonutti |
| 2003/0055500 A1 | 3/2003 | Fell et al. |
| 2003/0055501 A1 | 3/2003 | Fell et al. |
| 2003/0055502 A1 | 3/2003 | Lang et al. |
| 2003/0060882 A1 | 3/2003 | Fell et al. |

(56) References Cited

U.S. PATENT DOCUMENTS

| | | |
|---|---|---|
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0100907 A1 | 5/2003 | Rosa et al. |
| 2003/0100953 A1 | 5/2003 | Rosa et al. |
| 2003/0120347 A1 | 6/2003 | Steinberg |
| 2003/0158558 A1 | 8/2003 | Horn |
| 2003/0158606 A1 | 8/2003 | Coon et al. |
| 2003/0163137 A1 | 8/2003 | Smucker et al. |
| 2003/0173695 A1 | 9/2003 | Monkhouse et al. |
| 2003/0216669 A1 | 11/2003 | Lang et al. |
| 2003/0225457 A1 | 12/2003 | Justin et al. |
| 2003/0236521 A1 | 12/2003 | Brown et al. |
| 2003/0236526 A1 | 12/2003 | Van Hoeck et al. |
| 2004/0098133 A1 | 5/2004 | Carignan et al. |
| 2004/0102852 A1 | 5/2004 | Johnson et al. |
| 2004/0122521 A1 | 6/2004 | Lee et al. |
| 2004/0133276 A1 | 7/2004 | Lang et al. |
| 2004/0138754 A1 | 7/2004 | Lang et al. |
| 2004/0147927 A1 | 7/2004 | Tsougarakis et al. |
| 2004/0153079 A1 | 8/2004 | Tsougarakis et al. |
| 2004/0153162 A1 | 8/2004 | Sanford et al. |
| 2004/0153164 A1 | 8/2004 | Sanford et al. |
| 2004/0167390 A1 | 8/2004 | Alexander et al. |
| 2004/0167630 A1 | 8/2004 | Rolston |
| 2004/0193280 A1 | 9/2004 | Webster et al. |
| 2004/0204644 A1 | 10/2004 | Tsougarakis et al. |
| 2004/0204760 A1 | 10/2004 | Fitz et al. |
| 2004/0236424 A1 | 11/2004 | Berez et al. |
| 2004/0249386 A1 | 12/2004 | Faoro |
| 2005/0015153 A1 | 1/2005 | Goble et al. |
| 2005/0021039 A1 | 1/2005 | Cusick et al. |
| 2005/0043807 A1 | 2/2005 | Wood |
| 2005/0049603 A1 | 3/2005 | Calton et al. |
| 2005/0055028 A1 | 3/2005 | Haines |
| 2005/0085920 A1 | 4/2005 | Williamson |
| 2005/0107883 A1 | 5/2005 | Goodfried et al. |
| 2005/0107884 A1 | 5/2005 | Johnson et al. |
| 2005/0119664 A1 | 6/2005 | Carignan et al. |
| 2005/0143745 A1 | 6/2005 | Hodorek et al. |
| 2005/0148843 A1 | 7/2005 | Roose |
| 2005/0171545 A1 | 8/2005 | Walsh et al. |
| 2005/0171612 A1 | 8/2005 | Rolston |
| 2005/0192588 A1 | 9/2005 | Garcia |
| 2005/0216305 A1 | 9/2005 | Funderud |
| 2005/0234461 A1 | 10/2005 | Burdulis, Jr. et al. |
| 2005/0267584 A1 | 12/2005 | Burdulis et al. |
| 2006/0052795 A1 | 3/2006 | Burdulis et al. |
| 2006/0111722 A1 | 5/2006 | Bouadi |
| 2006/0149283 A1 | 7/2006 | May et al. |
| 2006/0200162 A1 | 9/2006 | Farling et al. |
| 2006/0235421 A1 | 10/2006 | Rosa et al. |
| 2007/0015995 A1 | 1/2007 | Lang |
| 2007/0073305 A1 | 3/2007 | Lionberger et al. |
| 2007/0118141 A1 | 5/2007 | Marchyn et al. |
| 2007/0162025 A1 | 7/2007 | Tornier et al. |
| 2007/0198022 A1 | 8/2007 | Lang et al. |
| 2007/0203430 A1 | 8/2007 | Lang et al. |
| 2007/0233151 A1 | 10/2007 | Chudik |
| 2007/0233156 A1 | 10/2007 | Metzger |
| 2007/0276224 A1 | 11/2007 | Lang et al. |
| 2007/0293868 A1 | 12/2007 | Delfosse et al. |
| 2008/0004709 A1 | 1/2008 | O'Neill et al. |
| 2008/0015433 A1 | 1/2008 | Alexander et al. |
| 2008/0025463 A1 | 1/2008 | Lang et al. |
| 2008/0031412 A1 | 2/2008 | Delfosse et al. |
| 2008/0058613 A1 | 3/2008 | Lang et al. |
| 2008/0058945 A1 | 3/2008 | Hajaj et al. |
| 2008/0114370 A1 | 5/2008 | Schoenefeld |
| 2008/0170659 A1 | 7/2008 | Lang et al. |
| 2008/0195109 A1 | 8/2008 | Hunter et al. |
| 2008/0195216 A1 | 8/2008 | Lang |
| 2008/0219412 A1 | 9/2008 | Lang |
| 2008/0243127 A1 | 10/2008 | Lang |
| 2008/0255565 A1 | 10/2008 | Fletcher |

| | | |
|---|---|---|
| 2008/0275452 A1 | 11/2008 | Lang et al. |
| 2008/0281328 A1 | 11/2008 | Lang et al. |
| 2008/0281329 A1 | 11/2008 | Lang et al. |
| 2008/0281426 A1 | 11/2008 | Fitz et al. |
| 2008/0287953 A1 | 11/2008 | Sers |
| 2009/0024131 A1 | 1/2009 | Metzger et al. |
| 2009/0043310 A1 | 2/2009 | Rasmussen |
| 2009/0076371 A1 | 3/2009 | Lang et al. |
| 2009/0087276 A1 | 4/2009 | Rose |
| 2009/0088753 A1 | 4/2009 | Aram et al. |
| 2009/0088758 A1 | 4/2009 | Bennett |
| 2009/0099567 A1 | 4/2009 | Zajac |
| 2009/0131941 A1 | 5/2009 | Park et al. |
| 2009/0131942 A1 | 5/2009 | Aker et al. |
| 2009/0149964 A1 | 6/2009 | May et al. |
| 2009/0198244 A1 | 8/2009 | Liebl |
| 2009/0204115 A1 | 8/2009 | Dees et al. |
| 2009/0222014 A1 | 9/2009 | Bojarski et al. |
| 2009/0307893 A1 | 12/2009 | Bojarski et al. |
| 2010/0160917 A1 | 6/2010 | Fitz et al. |
| 2010/0262150 A1 | 10/2010 | Lian |
| 2010/0274251 A1 | 10/2010 | Ranft |
| 2010/0281678 A1 | 11/2010 | Burdulis, Jr. et al. |
| 2010/0298894 A1 | 11/2010 | Bojarski et al. |
| 2010/0305573 A1 | 12/2010 | Fitz et al. |
| 2010/0305574 A1 | 12/2010 | Fitz et al. |
| 2010/0331847 A1 | 12/2010 | Wilkinson et al. |
| 2011/0066193 A1 | 3/2011 | Lang et al. |
| 2011/0071581 A1 | 3/2011 | Lang et al. |
| 2011/0213368 A1 | 9/2011 | Fitz et al. |
| 2011/0213373 A1 | 9/2011 | Fitz et al. |
| 2011/0213374 A1 | 9/2011 | Fitz et al. |
| 2011/0213377 A1 | 9/2011 | Lang et al. |
| 2011/0213427 A1 | 9/2011 | Fitz et al. |
| 2011/0213428 A1 | 9/2011 | Fitz et al. |
| 2011/0213429 A1 | 9/2011 | Lang et al. |
| 2011/0213430 A1 | 9/2011 | Lang et al. |
| 2011/0213431 A1 | 9/2011 | Fitz et al. |
| 2011/0218539 A1 | 9/2011 | Fitz et al. |
| 2011/0218542 A1 | 9/2011 | Lian et al. |
| 2011/0218584 A1 | 9/2011 | Fitz et al. |
| 2011/0230888 A1 | 9/2011 | Lang et al. |
| 2011/0238073 A1 | 9/2011 | Lang et al. |
| 2011/0313423 A1 | 12/2011 | Lang et al. |
| 2011/0319897 A1 | 12/2011 | Lang et al. |
| 2011/0319900 A1 | 12/2011 | Lang et al. |
| 2012/0029520 A1 | 2/2012 | Lang et al. |
| 2012/0041446 A1 | 2/2012 | Wong et al. |
| 2012/0066892 A1 | 3/2012 | Lang et al. |
| 2012/0071881 A1 | 3/2012 | Lang et al. |
| 2012/0071882 A1 | 3/2012 | Lang et al. |
| 2012/0071883 A1 | 3/2012 | Lang et al. |
| 2012/0072185 A1 | 3/2012 | Lang et al. |
| 2012/0101503 A1 | 4/2012 | Lang et al. |
| 2012/0143197 A1 | 6/2012 | Lang et al. |
| 2012/0151730 A1 | 6/2012 | Fitz et al. |
| 2012/0158001 A1 | 6/2012 | Burdulis, Jr. et al. |
| 2012/0191138 A1* | 7/2012 | Kiester .............. A61B 17/8004 |
| | | 606/281 |
| 2014/0243836 A1 | 8/2014 | Bake et al. |
| 2014/0270065 A9 | 9/2014 | Aram et al. |
| 2017/0112509 A9 | 4/2017 | Lancianese et al. |
| 2019/0083112 A1* | 3/2019 | Wallace .............. A61B 17/164 |
| 2019/0365394 A1 | 12/2019 | Abt et al. |
| 2021/0113222 A1* | 4/2021 | Khatibi .................. A61B 17/15 |
| 2021/0282790 A1 | 9/2021 | Sellman et al. |
| 2021/0378753 A1 | 12/2021 | Christen et al. |
| 2022/0022894 A1 | 1/2022 | Allard et al. |

FOREIGN PATENT DOCUMENTS

| | | |
|---|---|---|
| CN | 101111197 | 1/2008 |
| DE | 2306552 | 8/1974 |
| DE | 3516743 | 11/1986 |
| DE | 44 34 539 | 4/1996 |
| DE | 20303498 | 8/2003 |
| DE | 202008017199 | 3/2009 |
| DE | 202008017200 | 3/2009 |
| EP | 0377901 | 10/1989 |

(56) References Cited

FOREIGN PATENT DOCUMENTS

| EP | 0528080 | 2/1993 |
| EP | 0530804 | 10/1993 |
| EP | 0626156 | 11/1994 |
| EP | 0704193 | 4/1996 |
| EP | 0896825 | 2/1999 |
| EP | 0938869 | 9/1999 |
| EP | 0613380 | 12/1999 |
| EP | 0993807 | 4/2000 |
| EP | 1074229 | 2/2001 |
| EP | 1077253 | 2/2001 |
| EP | 1120087 | 8/2001 |
| EP | 1129675 | 9/2001 |
| EP | 1132061 | 9/2001 |
| EP | 0732091 | 12/2001 |
| EP | 0814731 | 8/2002 |
| EP | 1234552 | 8/2002 |
| EP | 1234555 | 8/2002 |
| EP | 0809987 | 10/2002 |
| EP | 0833620 | 10/2002 |
| FR | 2819714 | 7/2002 |
| GB | 1451283 | 9/1976 |
| GB | 2291355 | 1/1996 |
| GB | 2348373 | 10/2000 |
| JP | 8-173465 | 7/1996 |
| JP | 9-206322 | 8/1997 |
| JP | 2002-102236 | 4/2002 |
| JP | 2008-537689 | 9/2008 |
| WO | WO 87/02882 | 5/1987 |
| WO | WO 90/009769 | 9/1990 |
| WO | WO 93/004710 | 3/1993 |
| WO | WO 93/009819 | 5/1993 |
| WO | WO 93/025157 | 12/1993 |
| WO | WO 95/027450 | 10/1995 |
| WO | WO 95/028688 | 10/1995 |
| WO | WO 95/030390 | 11/1995 |
| WO | WO 95/032623 | 12/1995 |
| WO | WO 96/024302 | 8/1996 |
| WO | WO 97/025942 | 7/1997 |
| WO | WO 97/026847 | 7/1997 |
| WO | WO 97/027885 | 8/1997 |
| WO | WO 97/038676 | 10/1997 |
| WO | WO 98/012994 | 4/1998 |
| WO | WO 98/20816 | 5/1998 |
| WO | WO 98/030617 | 7/1998 |
| WO | WO 98/32384 | 7/1998 |
| WO | WO 99/002654 | 1/1999 |
| WO | WO 99/008598 | 2/1999 |
| WO | WO 99/008728 | 2/1999 |
| WO | WO 99/042061 | 8/1999 |
| WO | WO 99/047186 | 9/1999 |
| WO | WO 99/051719 | 10/1999 |
| WO | WO 99/056674 | 11/1999 |
| WO | WO 00/009179 | 2/2000 |
| WO | WO 00/015153 | 3/2000 |
| WO | WO 00/035346 | 6/2000 |
| WO | WO 00/048550 | 8/2000 |
| WO | WO 00/059411 | 10/2000 |
| WO | WO 00/074554 | 12/2000 |
| WO | WO 01/010356 | 2/2001 |
| WO | WO 01/017463 | 3/2001 |
| WO | WO 01/019254 | 3/2001 |
| WO | WO 01/035968 | 5/2001 |
| WO | WO 01/045764 | 6/2001 |
| WO | WO 01/068800 | 9/2001 |
| WO | WO 01/070142 | 9/2001 |
| WO | WO 01/091672 | 12/2001 |
| WO | WO 02/000270 | 1/2002 |
| WO | WO 02/000275 | 1/2002 |
| WO | WO 02/002158 | 1/2002 |
| WO | WO 02/022013 | 3/2002 |
| WO | WO 02/022014 | 3/2002 |
| WO | WO 02/023483 | 3/2002 |
| WO | WO 02/034310 | 5/2002 |
| WO | WO 02/036147 | 5/2002 |
| WO | WO 02/096268 | 12/2002 |
| WO | WO 03/007788 | 1/2003 |
| WO | WO 03/037192 | 5/2003 |
| WO | WO 03/047470 | 6/2003 |
| WO | WO 03/051210 | 6/2003 |
| WO | WO 03/055400 | 7/2003 |
| WO | WO 2003/065907 | 8/2003 |
| WO | WO 04/043305 | 5/2004 |
| WO | WO 04/049981 | 6/2004 |
| WO | WO 05/051239 | 6/2005 |
| WO | WO 05/051240 | 6/2005 |
| WO | WO 06/060795 | 6/2006 |
| WO | WO 06/127283 | 11/2006 |
| WO | WO 07/041375 | 4/2007 |
| WO | WO 2007/061983 | 5/2007 |
| WO | WO 07/092841 | 8/2007 |
| WO | WO 08/112996 | 9/2008 |
| WO | WO 08/157412 | 12/2008 |
| WO | WO 2009/001083 | 12/2008 |
| WO | WO 09/111639 | 9/2009 |
| WO | WO2009158522 | 12/2009 |
| WO | WO 2010/099142 | 9/2010 |
| WO | WO 2010/120346 | 10/2010 |
| WO | WO 2010/121147 | 10/2010 |
| WO | WO 2011/110374 | 9/2011 |
| WO | 2019022769 A1 | 1/2019 |
| WO | 2020239909 A2 | 12/2020 |
| WO | WO 2022015877 | 1/2022 |
| WO | WO 2022094052 | 5/2022 |

OTHER PUBLICATIONS

Argenson, et al., "Is There a Place for Patellofemoral Arthroplasty?, "Clinical Orthopaedics and Related Research No. 321, 1995, pp. 162-167.

Birnbaum, et al., "Computer-Assisted Orthopedic Surgery with Individual Templates and Comparison to Conventional Operation Method," Spine, Feb. 2001, pp. 365-369, vol. 26, No. 4.

Chelule, et al., "Computer Aided Design of Personalized Jigs in Total Knee Replacement," 3rd Annual Meeting of CAOS Int'l Proc., Jun. 18-21, 2003, pp. 58-59, Spain.

Dare, S., Bobyn, J., Drouin, G., Dussault, R., Gariepy, R., "Use of Computerized Tomography and Numerical Control Machining for the Fabrication of Custom Arthroplasty Prostheses." Second World Congress on Biomaterials, 10th Annual Meeting of the Society for Biomaterials, p. 233, Washington, D.C., Apr. 27-May 1, 1984.

De Winter, et al., "The Richards Type II Patellofemoral Arthroplasty," Acta Orthop Scand, 2001, pp. 487-490, 72(5).

Delp, et al., "A Graphics-Based Software System to Develop and Analyze Models of Musculoskeletal Structures," Comput. Biol. Med., 1995, pp. 21-34, vol. 25, No. 1.

Farrar, et al., "Computed Tomography Scan Scout Film for Measurement of Femoral Axis in Knee Arthroplasty," J. Arthroplasty, 1999, pp. 1030-1031, vol. 14, No. 8.

Final Official Action for U.S. Appl. No. 13/465,547, dated Feb. 26, 2014.

First Office Action for Japanese Patent Appln. No. 2011-552091, dated Oct. 25, 2013.

Froemel, et al., "Computer Assisted Template Based Navigation for Total Knee Replacement," Documents presented at CAOS on Jun. 17, 2001, 4 pages.

Hafez, et al., "Computer Assisted Total Knee Replacement: Could a Two-Piece Custom Template Replace the Complex Conventional Instrumentations?", 4th Annual Meeting of CAOS Int'l Proc., Jun. 16-19, 2004, pp. 63-64, Chicago.

Hafez, et al., "Computer-Assisted Total Hip Arthroplasty: The Present and the Future," Future Rheumatol., 2006, pp. 121-131, vol. 1.

Kim, et al., "Measurement of Femoral Neck Anteversion in 3D. Part 1: 3D Imaging Method," Med. and Biol. Eng. and Computing, 2000, pp. 603-609, vol. 38, No. 6.

Lam, et al., "X-Ray Diagnosis: A Physician's Approach," 1998, Title page and Table of Contents pages Only, ISBN 9813083247, Springer-Verlag publishers.

(56)         References Cited

OTHER PUBLICATIONS

Lam et al.. "VarusNalgus Alignment of the Femoral Component in Total Knee Arthroplasty," The Knee, 2003, pp. 237-241, vol. 10.

Lu, et al., "In Vitro Degradation of Porous poly(L-lactic acid) Foams," Biomaterials, Aug. 2000, pp. 1595-1605, 21(15).

Mahaisavariya, et al., "Morphological Study of the Proximal Femur: a New Method of Geometrical Assessment Using 3-Dimensional Reverse Engineering", Medical Engineering & Physics 24 (2002) pp. 617-622.

Marler, et al., "Soft-Tissue Augmentation with Injectable Alginate and Synegeneic Fibroblasts," Plastic & Reconstructive Surgery, May 2000 pp. 2049-2058, 105(6).

PCT/US2010/025143, International Preliminary Report on Patentability and Written Opinion, Sep. 9, 2011.

Portheine, et al., "Potentials of CT-based Planning and Template-based Procedure in Hip and Knee Surgery," Orth. Prac., 2000, pp. 786-791, vol. 36, English Translation with Certification.

Radermacher, "Computer Assisted Matching of Planning and Execution in Orthopedic Surgery," Slide Presentation, Nov. 29, 1993, 22 pages.

Radermacher, "Template Based Navigation—An Efficient Technique for Hip and Knee Surgery," CAOS First Asian Meet, Mar. 27-28, 2004, pp. 45-50, India.

Radermacher, et al., "Computer-Assisted Planning and Operation in Orthopedics," Orth. Prac. 36th Year, Dec. 2000, pp. 731-737, English Translation with Certification.

Rau, et al., "Small and Neat," Medical Tech. Int'l, 1993-94, pp. 65, 67 and 69.

Schkommadau, et al., "Clinical Experience With the Individual Template Technique," Orth. Prac., 2001, pp. 19-22, vol. 37, No. 1, English Translation with Certification.

Seel, et al., "Three-Dimensional Planning and Virtual Radiographs in Revision Total Hip Arthroplasty for Instability," Clinical Orthopaedics and Related Research, Jan. 2006, pp. 35-38, No. 442.

Slone, et al., "Body CT: a Practical Approach," 1999, Title page and Table of Contents pages Only, ISBN 007058219, McGraw-Hill.

Staudte, et al., "Computer-Assisted Operation Planning and Technique in Orthopedics," North Rhine-Westphalia Acad. for Sciences, Lecture N.444, 2000, 17 pages, ISSN 0944-8799, in German.

Staudte, et al., "Computer-Assisted Operation Planning and Technique in Orthopedics," North Rhine-Westphalia Acad. for Sciences, Lecture N.444, 2000, 34 pages, ISSN 0944-8799, English Translation with Certification.

Stauffer, et al., "The Macintosh Prosthesis. Prospective Clinical and Gait Evaluation," Arch. Surg., 1975, pp. 717-720, 110(6).

Stout, et al., "X-RAY Structure Determination: A Practical Guide," 1989, Title page and Table of Contents pages Only, ISBN 0471607118, John Wiley & Sons.

Tamez-Pena, et al., "MRIIsotropic Resolution Reconstruction from Two Orthogonal Scans," Proceedings of the SPIE—The International Society for Optical Engineering SOIE-OMT, 2001, pp. 87-97, vol. 4322.

Testi, et al., "Border Tracing Algorithm Implementation for the Femoral Geometry Reconstruction," Camp. Meth. and Programs in Biomed., 2001, pp. 175-182, vol. 65.

Vandeberg, et al., "Assessment of Knee Cartilage in Cadavers with Dual-Detector Spiral CT Arthrography and MR Imaging," Radiology, Feb. 2002, pp. 430-435, 222(2).

Wiese, et al., "Biomaterial Properties and Biocompatibility in Cell Culture of a Novel Self-Inflating Hydrogel Tissue Expander," J. Biomedical Materials Research Part A, Nov. 2000, pp. 179-188, 54(2).

Woolson, S., Fellingham, L., Dev, P., and Vassiliadis, A., "Three Dimensional Imaging of Bone from Analysis of Computed Tomography Data." Orthopedics, vol. 8, No. 10, pp. 1269-1273, Oct. 1985.

Yusof, et al., "Preparation and Characterization of Chitin Beads as a Wound Dressing Precursor," J. Biomedical Materials Research Part A, Oct. 2000, pp. 59-68, 54(1).

Examination Report issued in connection with corresponding Indian Patent Application No. 2004/KOLNP/2013, Nov. 27, 2018, 7 pages.

First Office Action issued in connection with corresponding Chinese Patent Application No. 201610973637.8, Nov. 28, 2018, 6 pages.

First Examination Repot issued in connection with corresponding Australian Patent Application No. 2018204063, Jul. 10, 2019, 2 pages.

Second Examination Report issued in connection with corresponding Australian Patent Application No. 2019261830, May 4, 2021, 9 pages.

First Examination Repot issued in connection with corresponding Australian Patent Application No. 201926183, Dec. 21, 2020, 4 pages.

Extended European Search Report issued in connection with corresponding European Patent Application No. 23172825.4, Dec. 1, 2023, 17 pages.

Partial Search Report issued in connection with European Patent Application No. 23172825, Sep. 13, 2023, 12 pages.

* cited by examiner

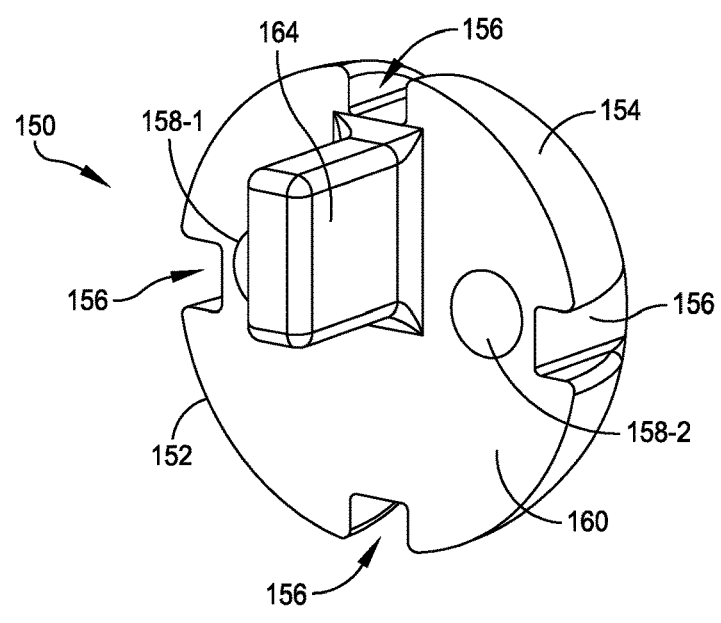
FIG. 3
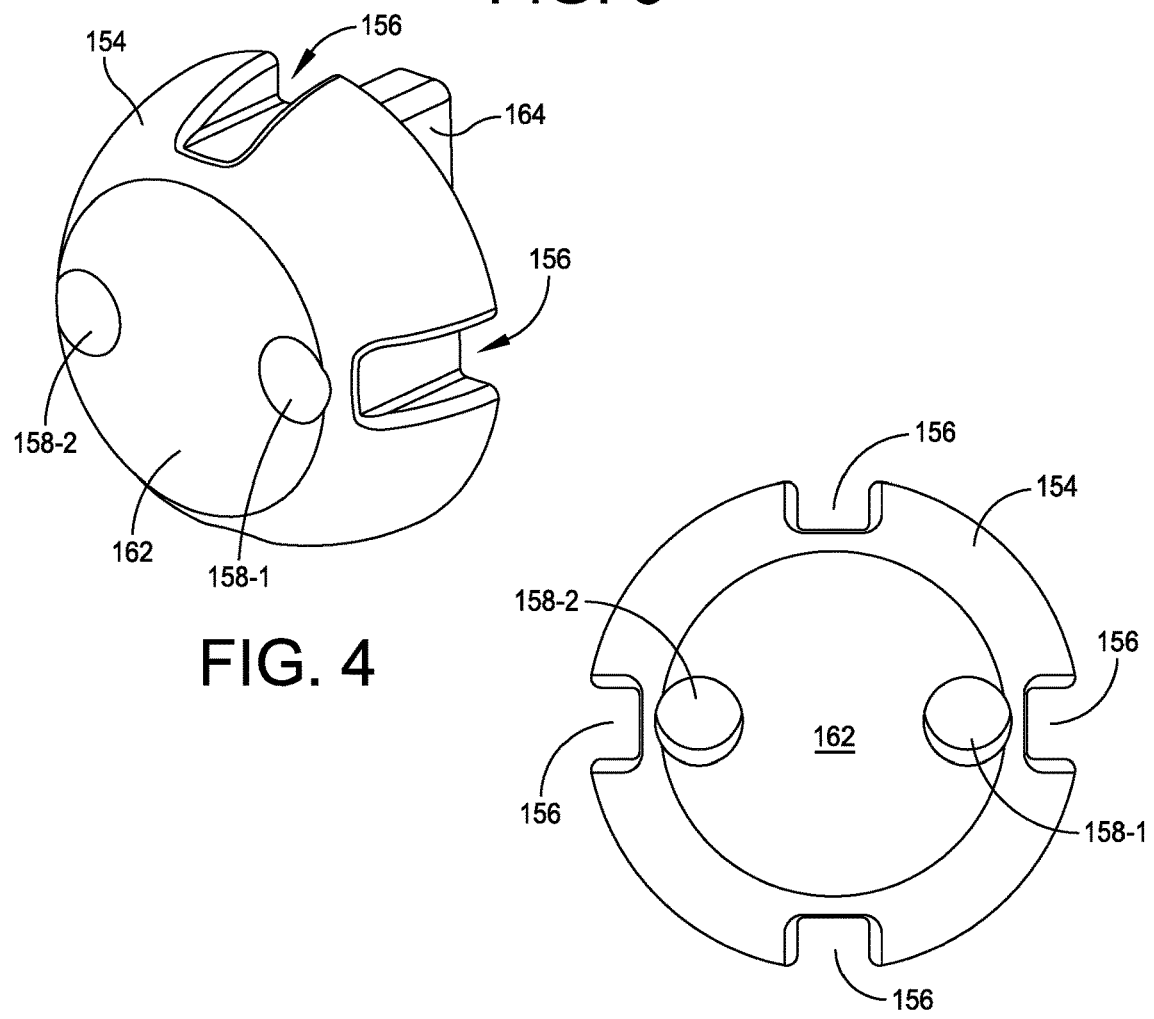
FIG. 4
FIG. 5

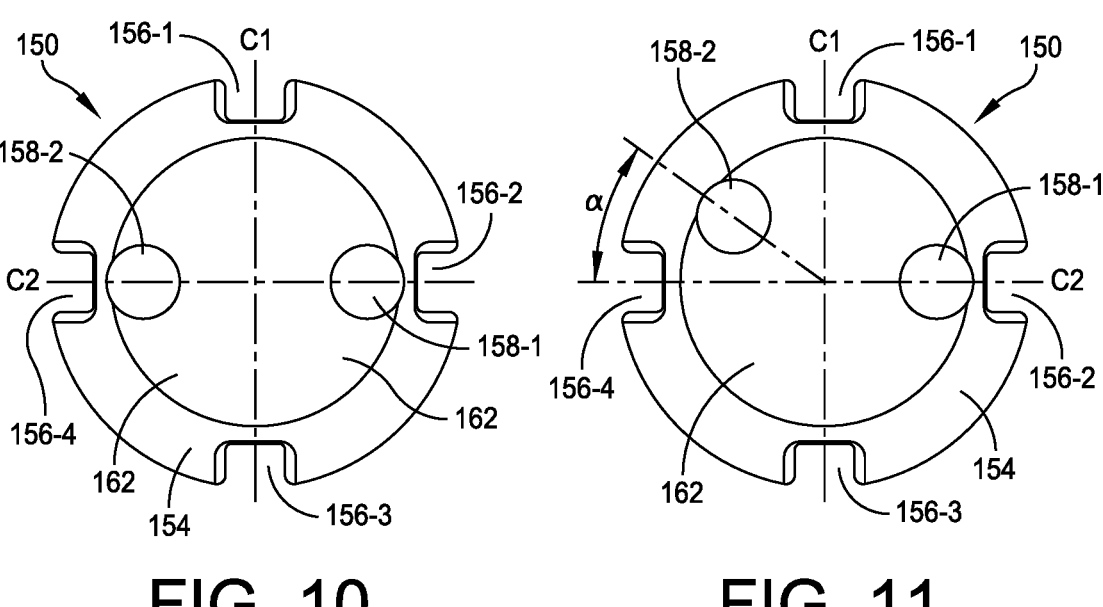
FIG. 10                    FIG. 11
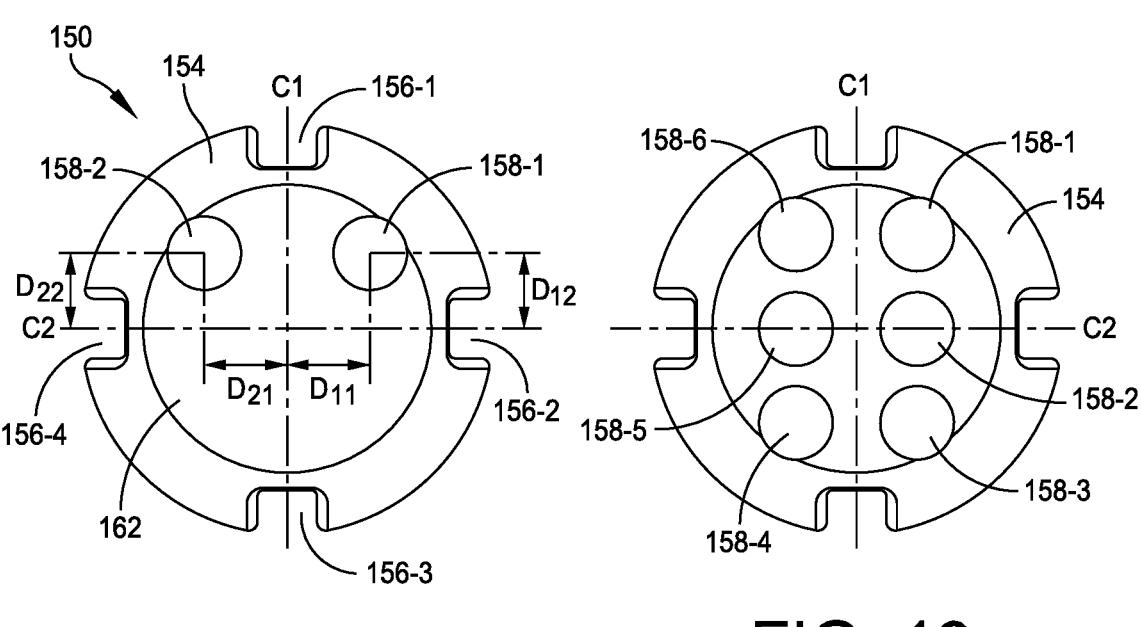
FIG. 12                    FIG. 13

150
164
156
166-1
158-1
154
156
158-2
166-2
156
160

154
164
150
158-2
166-2
156
160
162

156
150
154
166-1
166-2
164
158-1
158-2

INTRAOPERATIVE ADJUSTABLE GUIDES, SYSTEMS, AND METHODS

CROSS-REFERENCE TO RELATED APPLICATION

This application claims priority under 35 U.S.C. § 119(e) to U.S. Provisional Application No. 63/364,631, filed on May 13, 2022, the entire contents of which are incorporated herein by reference.

INCORPORATION BY REFERENCE

The entire disclosures of International Patent Application No. PCT/US2021/057014, filed Oct. 28, 2021; U.S. Pat. No. 10,413,308, issued Sep. 17, 2019; U.S. Pat. No. 9,402,640, issued Aug. 2, 2016; and U.S. Pat. No. 8,808,303, issued Aug. 19, 2014, are incorporated by reference herein.

FIELD

The disclosed guides, systems, and methods relate to surgical guides, systems, and methods. More specifically, the disclosed guides, systems, and methods relate to patient-specific surgical guides and systems that enable intraoperative adjustment by a surgeon or other user.

BACKGROUND

Total joint replacement prostheses typically include a specially designed jig or fixture to enable a surgeon to make accurate and precise bone resections in and around the joint being prepared to accept the prosthesis. The ultimate goal with any total joint prosthesis is to approximate the function and structure of the natural, healthy structures that the prosthesis is replacing. Should the prosthesis not be properly attached to the joint, i.e., an ankle or knee, the misalignment could result in discomfort to the patient, gait problems, or degradation of the prosthesis.

Accordingly, surgical devices and systems that provide for proper alignment of the bones of the joint are desirable.

SUMMARY

In some embodiments, a system can include a first component having a first body and a second component having a second body. The first body can have a first side and an opposed second side. The first side can have at least one patient-specific surface configured to engage at least one bone in a predetermined manner. The first body can also have a coupling element. The second body can be sized and configured to engage the coupling element to couple the second component to the first component. The second body can include at least one guide surface, and a position of the at least one guide surface can be configured to be adjusted relative to the first component intraoperatively.

A method can include placing a guide having at least one patient-specific surface into contact with at least one tissue of a patient and intraoperatively adjusting a location of at least one guide surface while the at least one patient-specific surface remains in contact with the at least one tissue.

BRIEF DESCRIPTION OF THE DRAWINGS

FIG. 3 is a front side isometric view of the adjustable component of the guide illustrated in FIG. 1 in accordance with some embodiments;

FIG. 4 is a rear side isometric view of the adjustable component of the guide illustrated in FIG. 1 in accordance with some embodiments;

FIG. 5 is a rear side plan view of the adjustable component of the guide illustrated in FIG. 1 in accordance with some embodiments;

FIG. 10 is a rear side plan view of another example of an adjustable component that can be used with a locating component in accordance with some embodiments;

FIG. 11 is a rear side plan view of another example of an adjustable component for use with a locating component in accordance with some embodiments;

FIG. 12 is a rear side plan view of another example of an adjustable component that can be used with a locating component in accordance with some embodiments;

FIG. 13 is a rear side plan view of another example of an adjustable component that can be used with a locating component in accordance with some embodiments;

DETAILED DESCRIPTION

Figure 1:
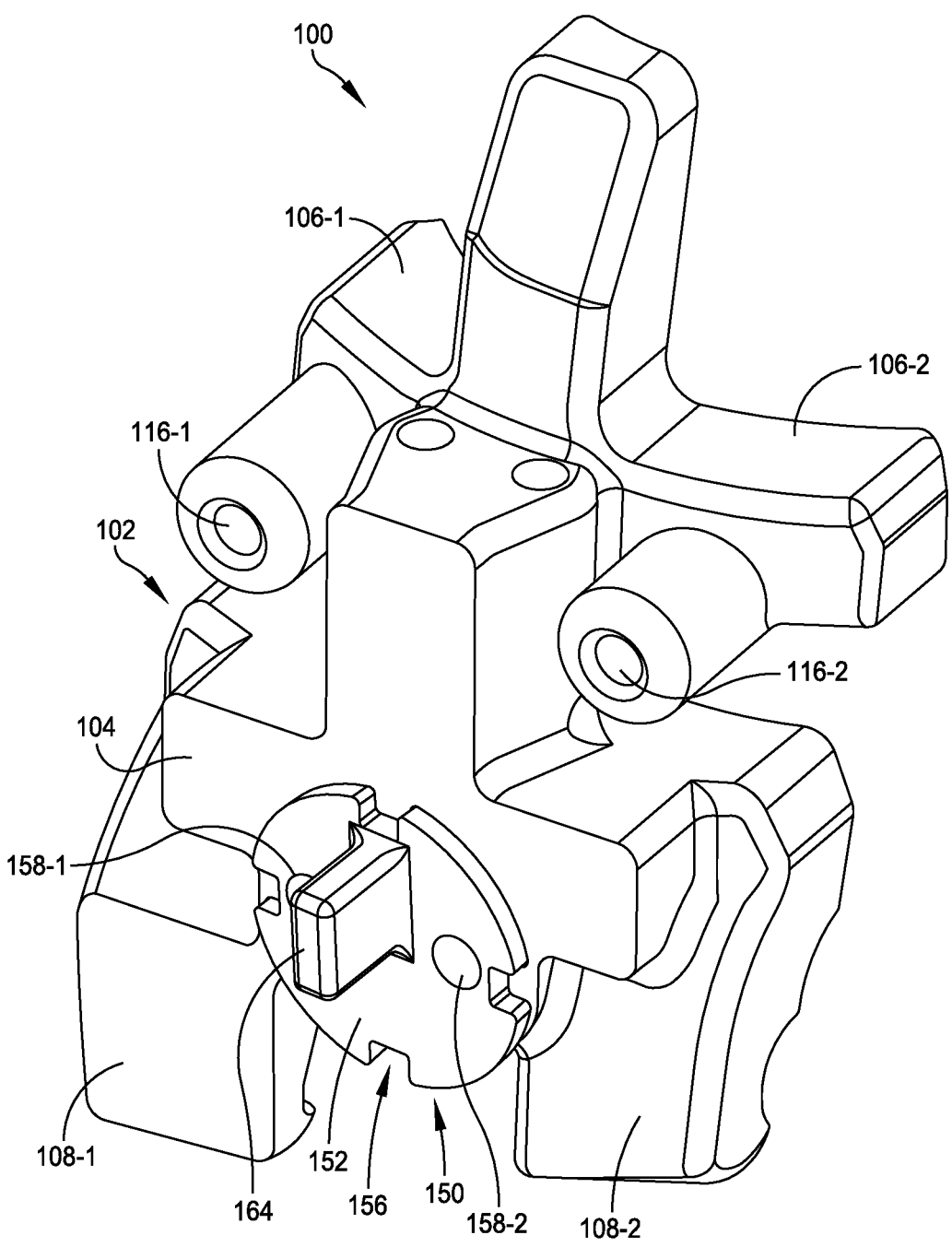
FIG. 1 is a front side isometric view of one example of a guide including a locating component and an adjustable component in accordance with some embodiments.

This description of the exemplary embodiments is intended to be read in connection with the accompanying drawings, which are to be considered part of the entire written description. It should be understood, however, that the present disclosure is not intended to be limited to the particular forms disclosed and that the drawings are not necessarily shown to scale. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, or otherwise, such that the connection allows the pertinent devices or components to operate with each other as intended by virtue of that relationship.

Patient-specific locator and/or cutting guides are created based on pre-operative imaging from which a surgeon or other medical professional prepares a preoperative plan. Conventional patient-specific locators and guides are designed to have one or more surfaces that are fabricated to mirror or be a negative of a surface of a patient's anatomy, such as bone and/or cartilage. The one or more patient-specific surfaces are designed to mate in a specific location on the patient's anatomy in a predefined manner, i.e., in accordance with the preoperative plan.

However, conventional patient-specific locators and mounts typically do not provide for deviation from the preoperative plan. Consequently, if a surgeon in the operating theater determines that the preoperative plan can not be suitable, such as due to unforeseen circumstances like ligament tension and/or issues in the preoperative imaging, then the only manner in which the surgeon can adjust the preoperative plan is by hand, i.e., without guidance from the patient-specific locator and/or guide.

To address such issues, the disclosed guides and systems can include multiple components, including at least one patient-specific locating component and one or more adjustable components for coupling to the patient-specific locating component, which advantageously enable a surgeon to make intraoperative adjustments to the preoperative plan while still providing the surgeon with guidance. For example, in some embodiments, a system can include a first component having a first body and a second component having a second body. The first body can have a first side and an opposed second side. The first side can have at least one patient-specific surface configured to engage at least one bone in a predetermined manner. The first body can also have a coupling element. The second body can be sized and configured to engage the coupling element to couple the second component to the first component. The second body can include at least one guide surface, and a position of the at least one guide surface can be configured to be adjusted relative to the first component intraoperatively.

In some embodiments, the at least one guide surface can include at least one hole sized and configured to receive a fixation device. The at least one hole can extend through the second body along an axis that is disposed perpendicular with respect to a plane defined by a first side of the second body. The at least one hole can be at least partially defined by a bushing that extends from the second body. The at least one hole can extend through the second body along an axis that is disposed at an oblique angle with respect to a plane defined by a first side of the second body. The at least one hole can be at least partially defined by a bushing that extends from the second body.

In some embodiments, the at least one guide surface can include at least one slot sized and configured to receive a cutting instrument. The at least one slot can include a first slot and a second slot. The first slot can be configured to guide a cutting instrument for resecting a first bone, and the second slot can be configured to guide a cutting instrument for resecting a second bone that is different from the first bone.

In some embodiments, the at least one guide surface can include at least one slot sized and configured to receive a cutting instrument.

In some embodiments, the coupling element can include an opening defined by the first body of the first component.

The second body can be sized and configured to be at least partially received within the opening.

In some embodiments, the second body can be configured to rotate freely within the opening about an axis defined by the opening.

In some embodiments, the first body can include indicia adjacent to the opening.

In some embodiments, the second body can be configured to be rotated selectively within the opening about an axis defined by the opening.

In some embodiments, the second body can define at least one groove, and the first body can include at least one protrusion. The at least one protrusion can be sized and configured to be received in the at least one groove.

In some embodiments, the second body can be configured to pivot about an axis that is oriented at an angle relative to the axis defined by the opening.

In some embodiments, the second body can include at least one protrusion, and the first body can define at least one groove. The at least one protrusion can be sized and configured to be received in the at least one groove.

In some embodiments, the second body can be configured to pivot about an axis that is oriented at an angle relative to the axis defined by the opening.

In some embodiments, the second body can include a first body portion and a second body portion. The second body portion can define the at least one guide surface and can be configured to move relative to the first body portion.

In some embodiments, the second body portion can be coupled to the first body portion by at least one pivot bar.

In some embodiments, the second body portion can be configured to move in first and second directions relative to the first body portion. The first and second directions can be orthogonal relative to one another.

In some embodiments, the second body can include a first body portion, a second body portion, and a third body portion. The first body portion, second body portion, and third body portion can collectively form a gimbal.

In some embodiments, the first body can include a first patient-specific surface configured to engage a first bone a second patient-specific surface configured to engage a second bone.

In some embodiments, the second component can define a first guide surface and a second guide surface. The first guide surface can be configured to be disposed adjacent to the first bone when the second component is coupled to the first component and the first patient-specific surface engages the first bone. The second guide surface can be configured to be disposed adjacent to the second bone when the second component is coupled to the first component and the second patient-specific surface engages the second bone.

The various guides disclosed herein can also be used to perform one or more methods. For example, in some embodiments, a method includes placing a guide having at least one patient-specific surface into contact with at least one tissue of a patient and intraoperatively adjusting a location of at least one guide surface while the at least one patient-specific surface remains in contact with the at least one tissue.

In some embodiments, after placing the guide and before intraoperatively adjusting a location of the at least one guide surface, at least one first fixation element can be inserted into the guide to fix a location of the guide relative to the at least one tissue of the patient.

In some embodiments, the guide can include a locating component and an adjustable component. The at least one first fixation element can be inserted into the locating component of the guide.

In some embodiments, at least one second fixation element can be inserted into the adjustable component after intraoperatively adjusting the location of the at least one guide surface.

In some embodiments, the at least one tissue can be engaged with a first surgical tool. The first surgical tool can be guided by the at least one guide surface. The at least one guide surface can define a hole, and the first surgical tool can be a drill. The at least one guide surface can define a slot, and the first surgical tool can be a saw.

In some embodiments, placing the guide into contact with at least one tissue of the patient includes can include placing a first patient-specific surface of the guide into contact with a first tissue placing a second patient-specific surface of the guide into contact with a second tissue. The second tissue can be different from the first tissue. The first tissue can be a first bone, and the second tissue can be a second bone. In some embodiments, the guide can extend across a joint located between the first bone and the second bone.

In some embodiments, the first bone can be engaged with a first surgical, which can be guided by a first guide surface. The first guide surface can define a first slot, and the first surgical tool can be a saw.

In some embodiments, the second bone can be engaged with the first surgical tool, which can be guided by a second guide surface. The second guide surface can be a second slot. The second guide surface can define a hole, and the second surgical tool can be a drill. The second guide surface can define a hole, and the second surgical tool can be at least one of a k-wire or a pin.

In some embodiments, the at least one tissue can be engaged with a first surgical tool, which can be guided by the at least one guide surface.

In some embodiments, adjusting the location of the guide surface can include rotating an adjustable component of the guide relative to a locating component of the guide.

In some embodiments, the guide can include a locating component and a first adjustable component. Adjusting the location of the guide surface can include replacing the first adjustable component with a second adjustable component.

In some embodiments, the method can include selecting the second adjustable component from a plurality of adjustable components.

In some embodiments, adjusting the location of the guide surface can include pivoting an adjustable component of the guide relative to a locating component of the guide.

In some embodiments, adjusting the location of the guide surface can include moving a first body portion of an adjustable component of the guide relative to a second body portion of the adjustable component of the guide.

Figure 2:
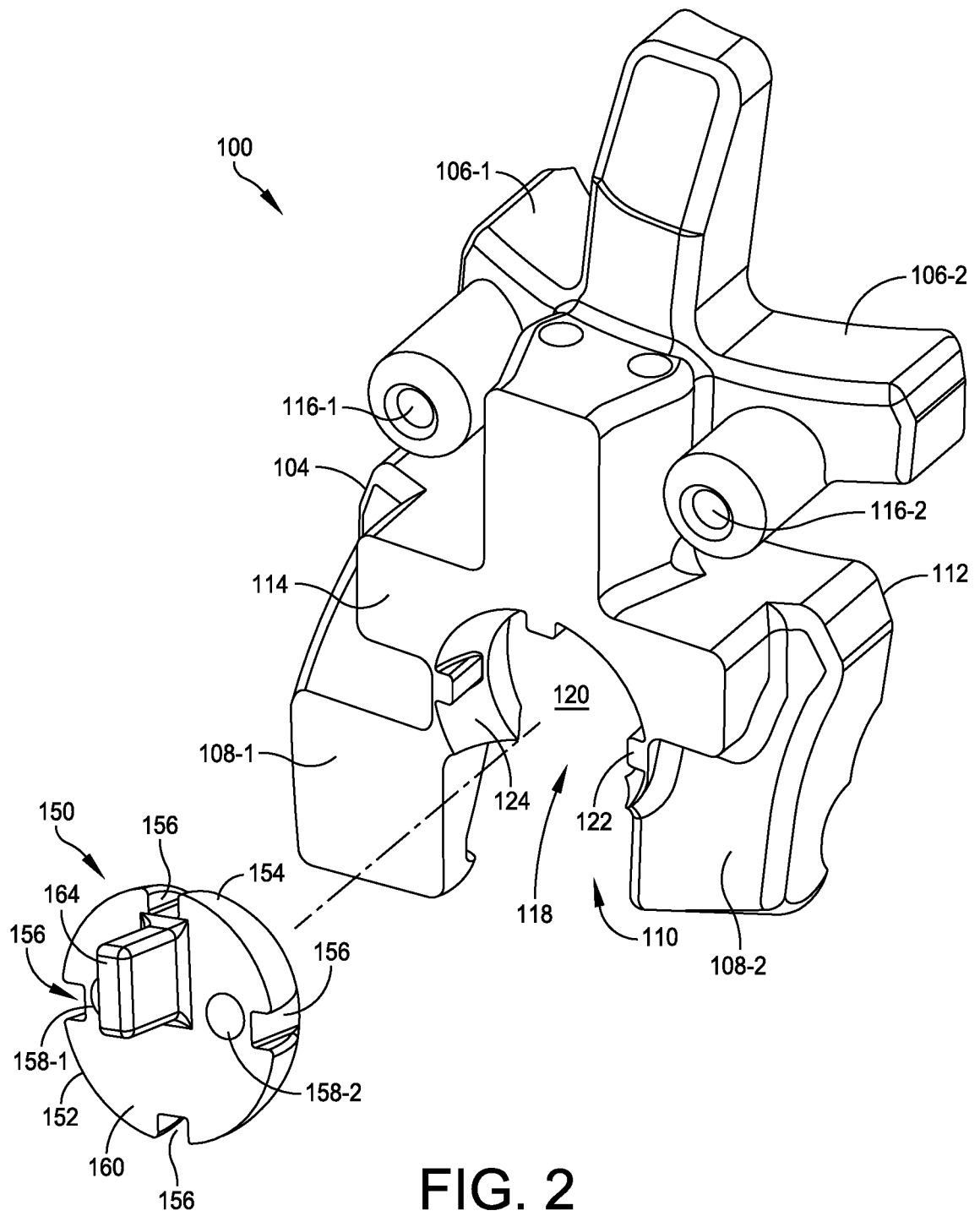
FIG. 2 is an exploded view of the guide illustrated in FIG. 1 in accordance with some embodiments.
Figure 6:
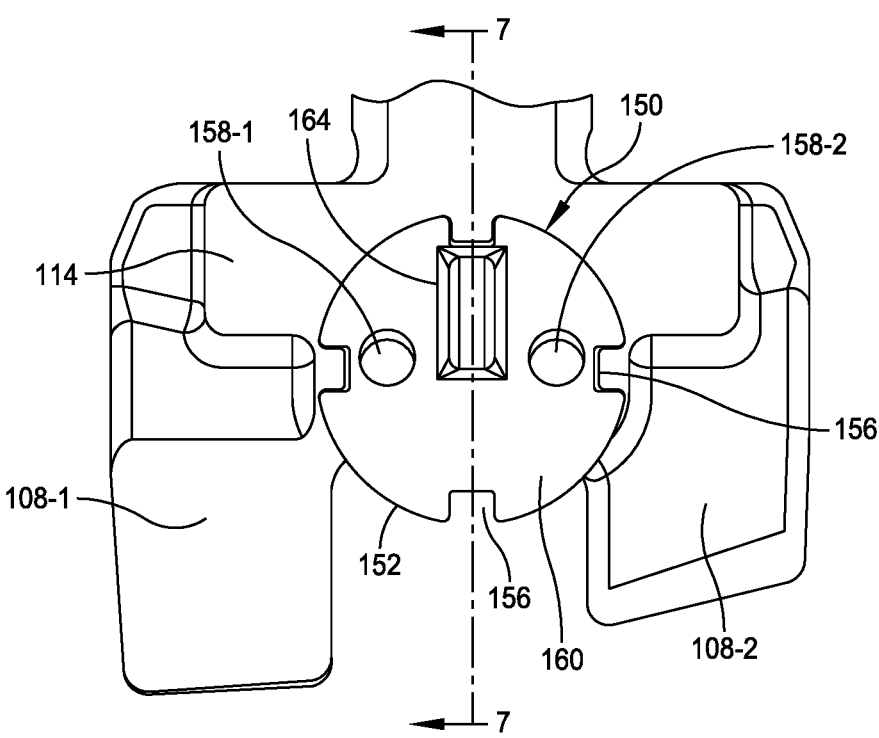
FIG. 6 is a partial front side plan view of the guide illustrated in FIG. 1 in accordance with some embodiments.
Figure 7:
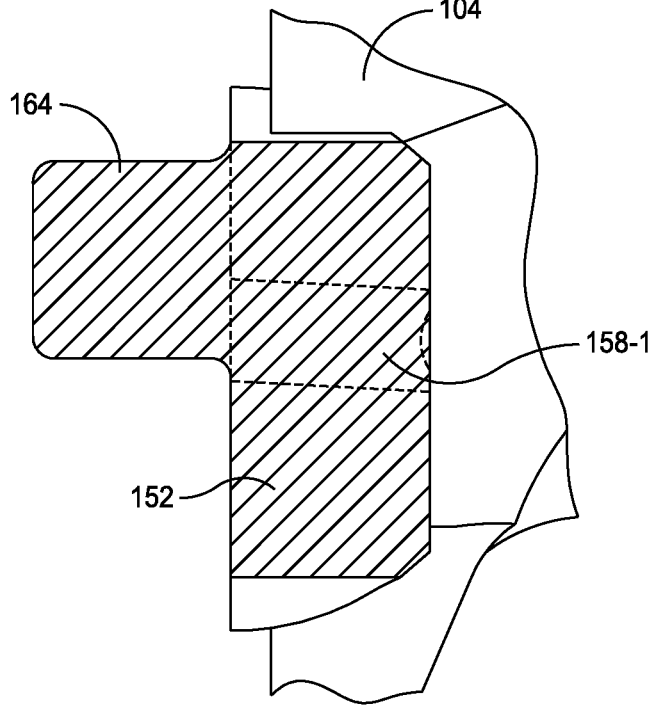
FIG. 7 is a cross sectional view of the guide illustrated in FIG. 1 taken along line 7-7 in FIG. 6 in accordance with some embodiments.

Turning now to the figures, FIGS. 1 and 2 illustrate one example of a patient-specific guide 100. Guide 100 can include a locating component 102, which can support or can be otherwise coupled to one or more adjustable components 150, which also can be referred to as a "guide insert." In some embodiments, the locating component 102 has a body 104 with a pair of outwardly extending arms 106-1, 106-2 (collectively "arms 106"). A pair of legs 108-1, 108-2 (collectively, "legs 108") can extend from the inferior end 110 of body 104. Body 104 can further include a first side 112, which can be a bone facing side, and an opposed second side 114. The bone-facing side 112 can include one or more patient specific surfaces that is based on preoperative imaging, as described in U.S. Pat. No. 5,768,134 issued to Swaelens et al., which is incorporated by reference herein in its entirety. In some embodiments, the locating component 102 can be formed from a medical-grade material that is capable of being 3D printed (e.g., additively manufactured), such as ABS (acrylonitrile butadiene styrene), PLA (polylactic acid), PETG (polyethylene terephthalate glycol), nylon, TPU (thermoplastic polyurethane), resin, and other suitable thermoplastics and thermosetting plastics, to list only a few possibilities. However, the locating component can be formed from other materials, including metals, ceramics, and other materials that are suitable for use in surgery as will be understood by one of ordinary skill in the art. In some embodiments, the locating component can be machined and/or formed using an additive manufacturing process, such as electron beam melting (EBM) or direct metal laser sintering (DMLS), to list only a few possibilities.

In some embodiments, the body defines one or more holes 116-1, 116-2 (collectively, "holes 116"). Holes 116 can be sized and configured to receive a k-wire, pin, or other fixation device for coupling the locating element 102 to one or more bones. The size of the holes 116 can be varied and are not necessarily shown to scale in the figures. In the example illustrated in FIGS. 1 and 2, each arm 106-1, 106-2 defines a respective hole 116-1, 116-2. It should be understood that body 104 can define other holes. For example, each leg 108-1, 108-2 can define a respective hole (not shown) to either increase the securement of locating component 102 to a first bone or to couple the locating component 102 to a second bone (e.g., a talus) while the holes 116 couple the locating component 102 to a first bone (e.g., a tibia). One of ordinary skill in the art will understand that additional holes can be provided and/or holes can be provided at other locations of the body 104.

The body 104 can further include one or more coupling element 118. In the example shown in FIGS. 1 and 2, the coupling element 118 can include an opening 120 defined by the body 104 and one or more protrusions 122 that extend inwardly into opening 120 from an angled or curved face 124. Although opening 120 is shown as having a circular shape, it should be understood that opening 120 can have other shapes, including polygonal, oval, conical, to list only a few possibilities. Further, while three protrusions 122 are shown extending inwardly into opening 120, fewer or more protrusions 122 can be provided as described in herein. Additionally or alternatively, one or more of the protrusions can be omitted or replaced with a channel or groove.

The one or more coupling elements 118 can be sized and configured to receive an adjustable component 150, such as one or more guide inserts 150 in an adjustable manner. For example, guide insert 150 can have a disc-shaped body 152 as best seen in FIGS. 2-5. The body 152 of guide insert 150 can be received within coupling element 118 such that guide insert 150 can move (e.g., rotate and/or pivot) in at least one direction within coupling element 118 and relative to locating component 102. For example, body 152 of guide insert 152 can include an angled or curved face 154 that is complementary to the shape of the angled or curved face 124 of the coupling element 118. In some embodiments, such as shown in the example illustrated in FIGS. 2-5, body 152 can include one or more channels or grooves 156 that are sized and configured to receive one of the protrusions 122. Protrusions 122 and grooves 156 provide for a keyed relationship and can prevent the body 152 of the guide insert 150 from moving in a first direction (e.g., rotating about a central axis defined by the opening 120) while allowing movement in a second direction (e.g., rotating about an axis that is perpendicular to the central axis defined by the opening 120). In some embodiments, the curved face 124 can taper or constrict to prevent downward translation of the guide insert 150 and the corresponding curved face 154, thereby constraining the modular guide insert in a seated position within the body 104. The guide insert can be locked, pinned, clipped or fastened into the seated position in a releasable or semi-permanent connection wherein the use of the cutting guides or drills does not dis-associate the connection beyond clinically desired restraints.

The location of the protrusions 122 along the angled or curved face 124 and/or the location of the channel or grooves 156 along body 152 can be selected to provide a predetermined amount of adjustment between the guide insert 152 and the locating component 102. However, in some embodiments, the interface between coupling element 118 and the body 152 of guide insert 150 can allow for unconstrained adjustment, which allows guide insert 150 to be rotated in a complete circle within coupling element 118 as described herein. Further, while the body 152 of guide insert 150 is shown as being able to fit only partially within coupling element 118, it should be understood that body 152 can be configured such that the entirety of the body 152 can be received within the coupling element 118.

Figure 21:
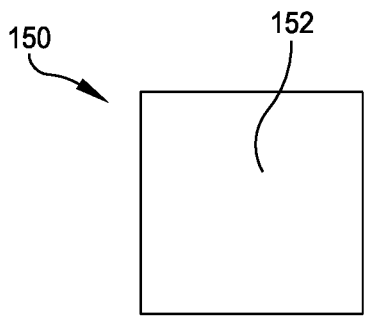
FIG. 21 is a schematic representation of one example of a shape of an adjustable component in accordance with some embodiments.
Figure 22:
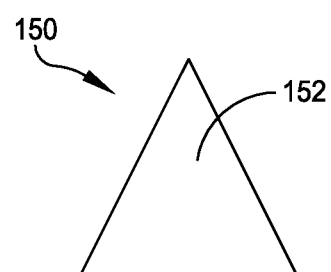
FIG. 22 is a schematic representation of another example of a shape of an adjustable component in accordance with some embodiments.
Figure 23:
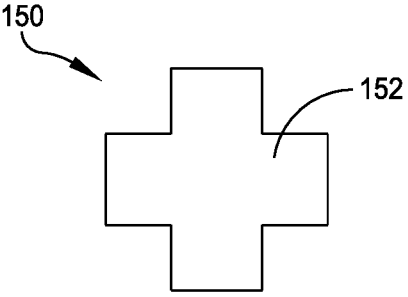
FIG. 23 is a schematic representation of another example of a shape of an adjustable component in accordance with some embodiments.
Figure 24:
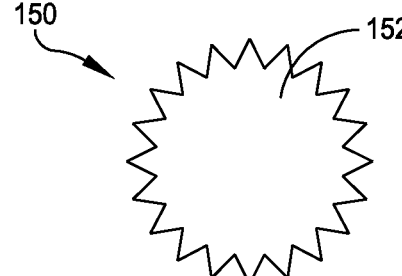
FIG. 24 is a schematic representation of another example of a shape of an adjustable component in accordance with some embodiments.

The body 152 of guide insert (e.g., adjustable component) 150 can have a shape other than a circular disk. For example, the body 152 can be shaped as a rectangular or square (FIG. 21), triangular (FIG. 22), cruciform (FIG. 23), or gear shaped (FIG. 24), to list one a few possibilities. It should be understood that the coupling element 118 can have a complementary shape to the body 152 of the guide insert such that the guide insert 150 can be coupled to the locating component 102. In some embodiments, the guide insert can be configured to be moved (e.g., rotated, pivoted, and/or repositioned) relative to the locating component 102. However, in some embodiments, as described below, the guide insert 150 can be coupled to locating component in a single orientation, but permit guide apertures and surfaces to be repositioned.

Guide insert 150 can include one or more guide apertures or surfaces 158 that can be used to facilitate a surgical process. For example, in the embodiment illustrated in FIGS. 2-5, the body 152 of guide insert 150 is shown as including two pin guides 158-1, 158-2 (collectively, "pin guides 158"). Pin guides 158 can extend from a first side 160 of body 152 to an opposed second side 162 as best seen in FIGS. 4-5. In the example illustrated in FIGS. 2-5 and 10, the pin guides 158 are shown disposed on either side of a tab 164 that extends away from a planar surface defined by the side 160 and positioned along a first center line C1 that bisects the body 152 in a first direction and are offset from a second center line that bisects the body 152 in a second direction that is perpendicular to the first direction as best seen in FIG. 10. In some embodiments, the centerline C1 extends through a first pair of channel or grooves 156 (e.g., channels 156-1 and 156-3) and centerline C2 extends through a second pair of channel or grooves 156 (e.g., channels 156-2 and 156-4), as shown in FIG. 10.

However, it should be understood that the number of pin guides 158 can be varied along with the location of the pin guides 158. For example, FIG. 11 illustrates an example of a guide insert 150 in which a first pin guide 158-1 is positioned along center line C2 and second pin guide 158-2 is positioned at an angle α from center line C2. In the example illustrated in FIG. 12, the first and second pin guides 158-1, 158-2 are both offset from the first and second centerlines C1 and C2. In some embodiments, the first pin guide 158-1 is offset from the first centerline by a distance $D_{11}$ and is offset from the second centerline C2 by a distance $D_{12}$. The second pin guide 158-2 can be offset from the first centerline C1 by a distance $D_{21}$ and can be offset from the second centerline C2 by a distance $D_{22}$. As will be understood by one of ordinary skill in the art, the distances $D_{11}$, $D_{12}$, $D_{21}$, and $D_{22}$ can be the same or different from one another.

FIG. 13 illustrates another example of a guide insert 150 having a plurality of pin guides 156. In the example illustrated in FIG. 13, the guide insert 150 is provided with six pin guides 158 all disposed at a distance from the first centerline C1. Four of the pin guides 158-1, 158-3, 158-4, 158-6 are disposed at a distance from the second center line C2, and two of the pin guides 158-2, 158-5 are disposed along the second center line C2. It should be understood that the locations of the pin guides 158 and the number of pin guides 158 can be varied. For example, the pin guides 158 can be arranged in a circular, triangular, rectangular, or other geometric arrangement.

Figures 14, 15, 16:
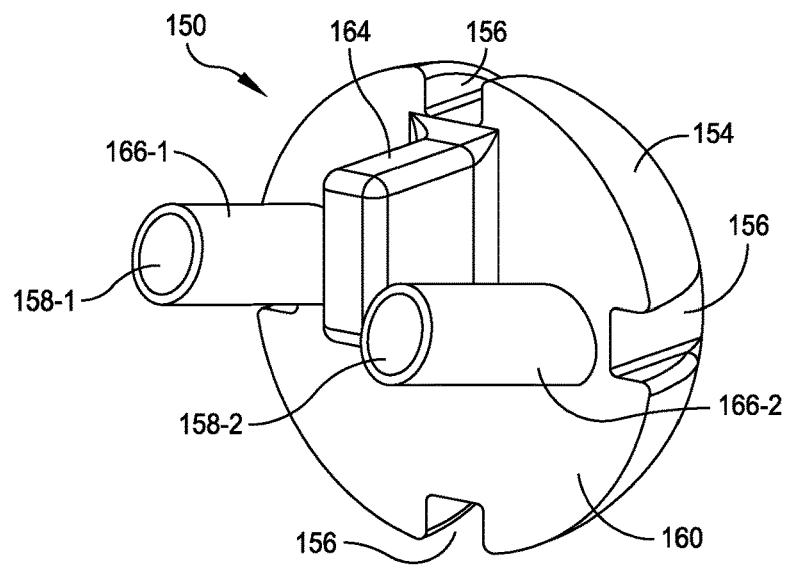
FIG. 14 is an isometric view of another example of an adjustable component that can be used with a locating component in accordance with some embodiments.
FIG. 15 is a side view of the adjustable component illustrated in FIG. 14 in accordance with some embodiments.
FIG. 16 is a top side view of the adjustable component illustrated in FIG. 14 in accordance with some embodiments.
Figures 17, 18:
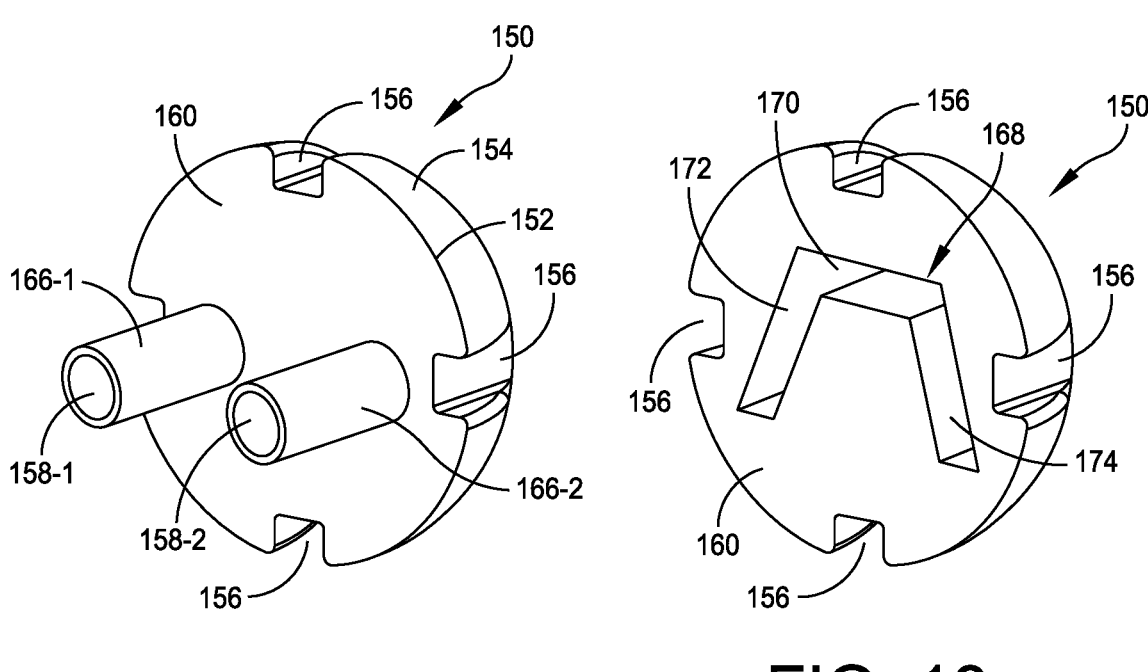
FIG. 17 is an isometric view of another example of an adjustable component that can be used with a locating component in accordance with some embodiments.
FIG. 18 is an isometric view of another example of an adjustable component that can be used with a locating component in accordance with some embodiments.

In some embodiments, pin guides 158 can include bushings to provide increased stability. For example, FIGS. 14-16 illustrate one example of a guide insert 150 including a pair of pin guides 158-1, 158-2 each with a respective bushing 166-1, 166-2 (collectively, "bushings 166"). As shown in FIGS. 14-16, the bushings 166 extend away from side 160. In some embodiments, such as the example illustrated in FIGS. 14-16, the bushings 166 and corresponding pin guides 158 are disposed at an oblique angle with respect to a planar surface defined by one of the sides 160, 162. In some embodiments, the bushings 166 and/or corresponding pin guides 158 can be disposed at other angles, including a right angle with respect to a planar surface defined by one of the sides 160, 162, as shown in FIG. 17. In some embodiments, a system or kit can be provided with a locating component 102 and one or more guide inserts 150, with each guide insert 150 being different. For example, a locating component 102 can be provided with multiple guide inserts 150 with each guide insert 150 having pin guides 158 oriented at different angles (e.g., 90°, 85°, 80°, 75°, 70°, 65°, 60°, 55°, 50°, 45°, etc.) relative to a planar surface of the guide. Although increments of 5° degrees are provided as an example, it should be understood that other increments can be provided in a system and/or kit.

As noted above, the pin guides 158 are sized and configured to receive a pin, k-wire, or other fixation element, as will be understood by one of ordinary skill in the art. Additionally or alternatively, the opening of the pin guides 158 can be sized and configured to receive a bone removal tool, such as a drill bit or rotary cutting tool. In some embodiments, the body 152 of the guide insert 150 can be formed from a material that is more rigid and/or durable than the material from which the locating component is formed. For example, the guide insert body 152 can be formed from a medical-grade metal, such as titanium, stainless steel, cobalt, and/or chromium, to list only a few possible materials. Further, the guide insert body 152 can be machined and/or formed using an additive manufacturing process, such as electron beam melting (EBM) or direct metal laser sintering (DMLS), to list only a few possibilities.

Advantageously, the coupling between locating component 102 and guide insert 150 allows a surgeon or other user to adjust a location at which a fixation element and/or bone removal tool is applied to bone. As noted above, the user can make the decision to adjust a relative position between the guide insert 150 and locating component 102 intraoperatively in response to viewing the surgical site.

Figure 8:
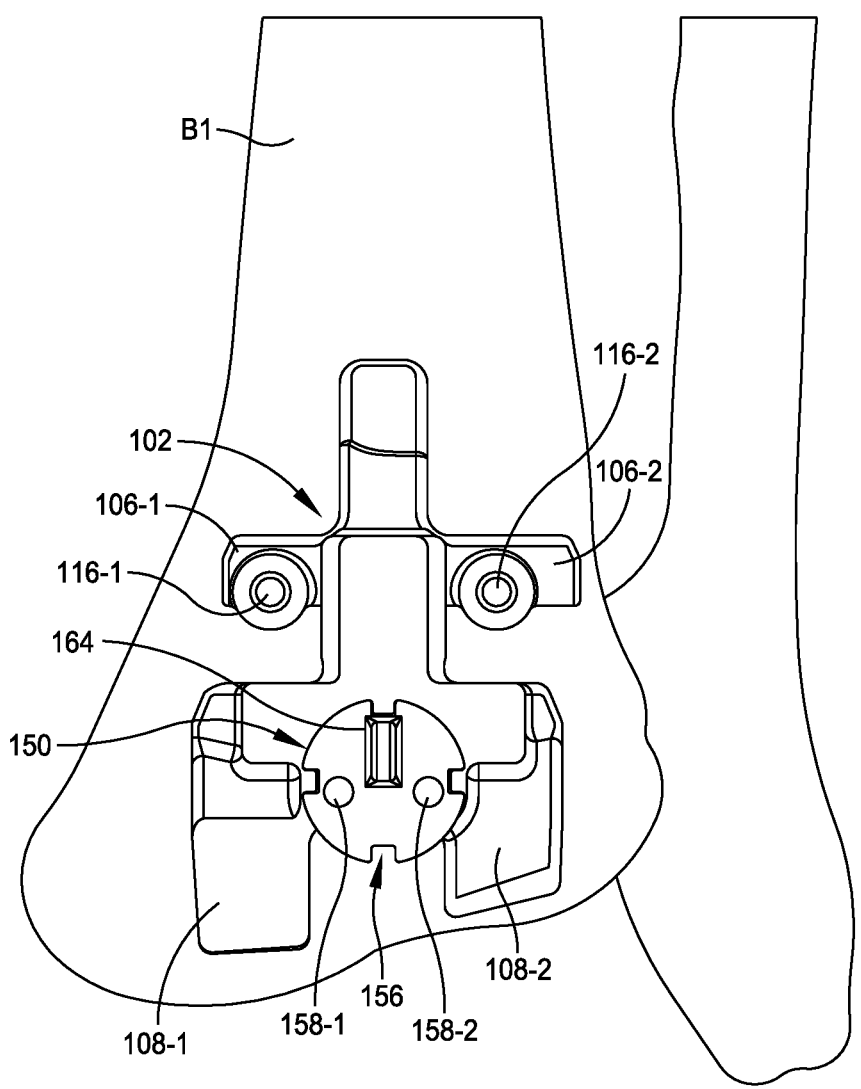
FIG. 8 is one example of a front side view of the guide illustrated in FIG. 1 positioned on a first bone in accordance with some embodiments.

In some embodiments, one or more fixation devices can be inserted into the pin guides 150 to establish a reference location that will serve the basis for placing one or more other guides, such as described in U.S. Pat. No. 10,413,308, which was incorporated by reference above. In such embodiments, the locating component 102 and guide insert 150 can be removed from their engagement with the bone once the one or more fixation devices have been placed and then other guides or fixtures can be coupled to the fixation devices. For example, FIG. 8 shows an example in which a guide 100, including a locating device 102 and a guide insert 150, is placed on a bone B1, which in this example is a tibia. One or more fixation elements can be inserted into the pin guides 158, and then the guide 100 can be removed from its engagement with the bone B1 by sliding the guide 100 off the fixation elements.

Figures 19, 20:
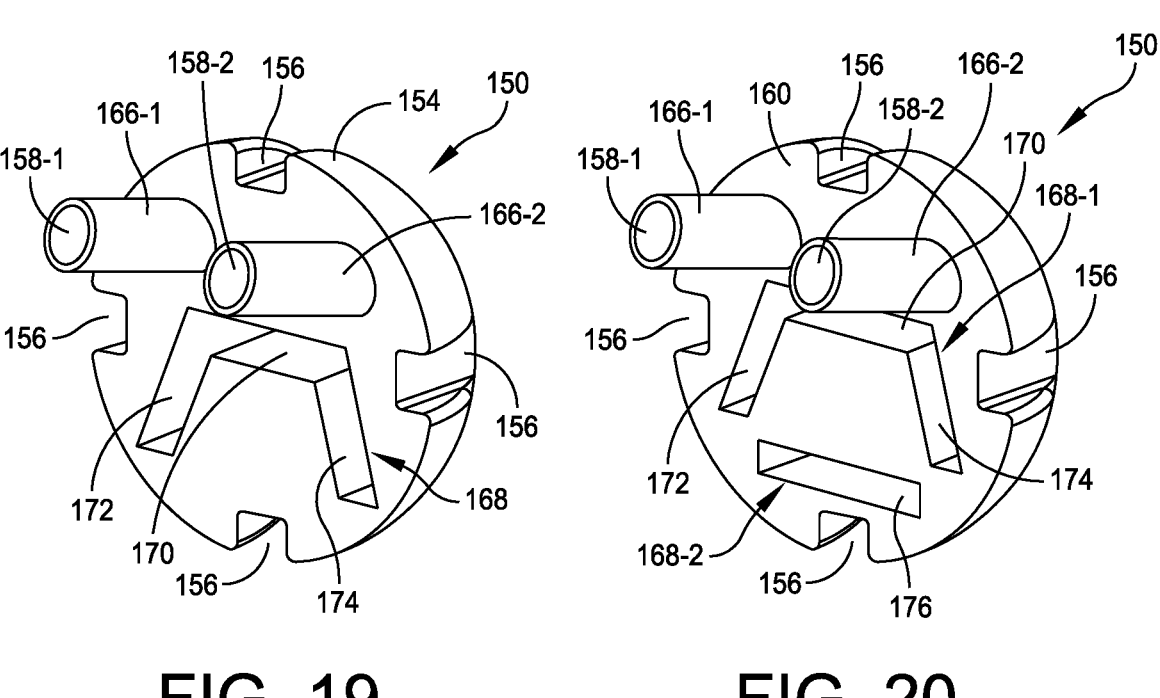
FIG. 19 is an isometric view of another example of an adjustable component that can be used with a locating component in accordance with some embodiments.
FIG. 20 is an isometric view of another example of an adjustable component that can be used with a locating component in accordance with some embodiments.

The guide can also be used to guide tools and instruments other than fixation devices. For example, FIGS. 18-20 illustrate examples of guide inserts including at least one cutting guide 168 to facilitate the removal of bone or tissue. Referring first to FIG. 18, the cutting guide 168 can include a transverse slot 170 with a first angled slot 172 extending from a first end of the transverse slot 170 and a second angled slot 174 extending from a second end of the transverse slot 170. As noted above, the size and orientation of the slots shown in the figures is not necessarily to scale, and the number, orientation, and/or size of the slots can be varied. The cutting guide 168 can be sized and configured to receive a cutting tool, such as a saw blade or rotary cutting tool, for cutting bone. It should be understood that the size and shape of cutting guide 168 can be varied and that a system and/or kit can be provided with multiple guide inserts 150 each having a cutting guide 168 with a different shape and/or size. For example, the different shapes and/or size of the cutting guides 168 can correspond to a respective implant that can be available to be implanted in a patient. The scale, pattern, depth, thickness, and orientation of the pin guides 158 and transverse slot 170 can be varied as is understood by one skilled in the art.

FIG. 19 illustrates another example of a guide insert 150 in accordance with some embodiments. The guide insert 150 illustrated in FIG. 19 includes a cutting guide 168 and pin guides 158. Providing the pin guides 158 along with the cutting guide allows the user to fix the position of the guide insert 150 relative to the bone. In some embodiments, once one or more fixation devices are inserted into the one or more pin guides 158, the assemblage of the locating component 102 and guide insert 150 can be slid off of the fixation devices, and then the guide insert 150 can be slid back onto the fixation devices prior to the bone being resected using a cutting tool guided by the cutting guide 168. However, in some embodiments, the locating device 102 and guide insert 150 can remain positioned on the bone during the resection, as described in PCT/US2021/057014, which was incorporated by reference above.

FIG. 20 illustrates another example of a guide insert including one or more pin guides and one or more cutting guides. As shown in FIG. 20, guide insert 150 includes pin guides 158-1, 158-1 and cutting guides 168-1, 168-2 (collectively, "cutting guides 168"). The pin guides 158 and first cutting guide 168-1 can be similar to the pin guides 158 and cutting guide 168 described above with respect to the guide insert illustrated in FIG. 19. Cutting guide 168-2 can include a slot 176 that can extend parallel to transverse slot 170, although slot 176 can be oriented in a non-parallel fashion relative to transverse slot 170.

Figure 9:
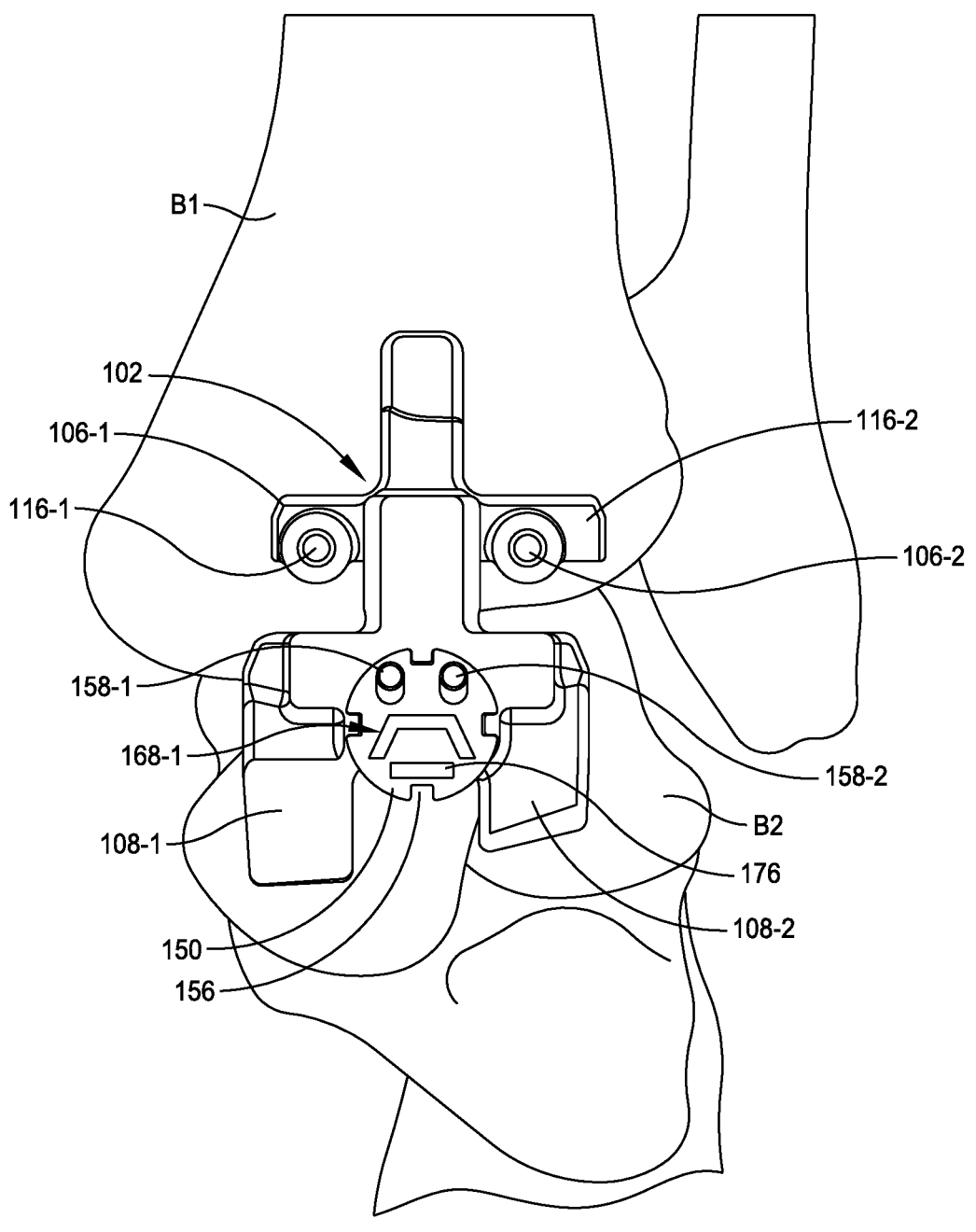
FIG. 9 is one example of a front side view of a guide positioned on first and second bones such that the guide is disposed across a joint in accordance with some embodiments.

In some embodiments, the pin guides 158 and first cutting guide 168-1 can be configured to be located relative to a first bone B1, e.g., a tibia, and the second cutting guide 168-2 can be configured to be located relative to a second bone B2, e.g., a talus, as shown in FIG. 9. For example, the first cutting guide 168-1 can be configured to guide a cutting tool for resecting a tibia, and the second cutting guide 168-2 can be configured to guide a cutting tool for resecting a talus. However, it should be understood that the locating components and guide inserts can be used with other bones and/or joints, including the knee, shoulder, hip, elbow, and wrist, to list only a few possibilities.

Guide insert 150 can include one or more guide apertures or surfaces 158 that can be used to facilitate a surgical process. For example, in the embodiment illustrated in FIGS. 2-5, the body 152 of guide insert 150 is shown as including two pin guides 158-1, 158-2 (collectively, "pin guides 158"). Pin guides 158 can extend from a first side 160 of body 152 to an opposed second side 162 as best seen in FIGS. 4-5. In the example illustrated in FIGS. 2-5 and 10, the pin guides 158 are shown disposed on either side of a tab 164 that extends away from a planar surface defined by the side 160 and positioned along a first center line C1 that bisects the body 152 in a first direction and are offset from a second center line that bisects the body 152 in a second direction that is perpendicular to the first direction as best seen in FIG. 10. In some embodiments, the centerline C1 extends through a first pair of channel or grooves 156 (e.g., channels 156-1 and 156-3) and centerline C2 extends through a second pair of channel or grooves 156 (e.g., channels 156-2 and 156-4), as shown in FIG. 10.

However, it should be understood that the number of pin guides 158 can be varied along with the location of the pin guides 158. For example, FIG. 11 illustrates an example of a guide insert 150 in which a first pin guide 158-1 is positioned along centerline C2 and second pin guide 158-2 is positioned at an angle α from centerline C2. In the example illustrated in FIG. 12, the first and second pin guides 158-1, 158-2 are both offset from the first and second centerlines C1 and C2. In some embodiments, the first pin guide 158-1 is offset from the first centerline by a distance $D_{11}$ and is offset from the second centerline C2 by a distance $D_{12}$. The second pin guide 158-2 can be offset from the first centerline C1 by a distance $D_{21}$ and can be offset from the second centerline C2 by a distance $D_{22}$. As will be understood by one of ordinary skill in the art, the distances $D_{11}$, $D_{12}$, $D_{21}$, and $D_{22}$ can be the same or different from one another.

FIG. 13 illustrates another example of a guide insert 150 having a plurality of pin guides 156. In the example illustrated in FIG. 13, the guide insert 150 is provided with six pin guides 158 all disposed at a distance from the first centerline C1. Four of the pin guides 158-1, 158-3, 158-4, 158-6 are disposed at a distance from the second center line C2, and two of the pin guides 158-2, 158-5 are disposed along the second center line C2. It should be understood that the locations of the pin guides 158 and the number of pin guides 158 can be varied. For example, the pin guides 158 can be arranged in a circular, triangular, rectangular, or other geometric arrangement.

Figure 25:
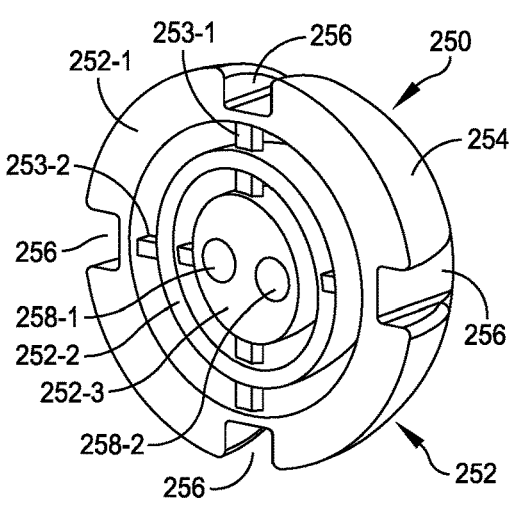
FIG. 25 is a front side isometric view of another example of an adjustable component that can be used with a locating component in accordance with some embodiments.
Figure 26:
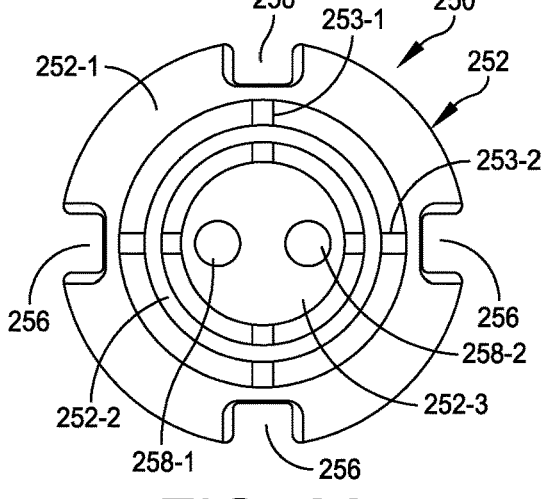
FIG. 26 is a front side view of the adjustable component illustrated in FIG. 25 in accordance with some embodiments.

As noted above, guide inserts can be configured to be coupled to a locator component in a single orientation while providing a surgeon or other medical professional or user with the ability to adjust a location and/or orientation of a guide structure intraoperatively. Examples of such guide inserts are illustrated in FIGS. 25-31. Turning first to FIGS. 25 and 26, guide insert 250 includes a body 252 including multiple portions that are movably coupled to one another. More particularly, guide insert 250 illustrated in FIGS. 25 and 26 includes a first body portion 251-1, which can be referred to as an outer body portion and have a circular shape, a second body portion 252-2, which can be referred to as a middle body portion and have a circular shape, and a third body portion 252-3, which can be referred to as an inner body portion and have a circular shape. While three body portions are shown, it should be understood that fewer or more body portions can be provided.

Body portions 252-1, 252-2, 252-3 (collectively, "body portions 252" or "body 252") can be pivotably coupled to one another about pivot bars 253-1, 253-2 (collectively, "pivot bars 253") to form a gimbal structure. In the example illustrated in FIGS. 25 and 26, body portion 252-1 includes a curved or angled face 254 and one or more channels or grooves 256 defined by the curved or angled face 254. Face 254 can facilitate coupling to a coupling element, such as the coupling element 118 described above, or can be omitted depending on the configuration of the coupling element 118. Similarly, the channels or grooves 256 can be configured to receive a protrusion 122 of coupling element. The channels or grooves 256 can permit movement of body portion 252-1 relative to the locating component 102, or channels or grooves 256 can prevent movement of the body portion 252-1 relative to the locating component 102.

Inner body portion 252-3 is shown as defining a pair of spaced-apart guide apertures 258-1, 258-2 (collectively, "guide apertures 258"), which can be sized and configured to receive a fixation element or device (e.g., k-wire or pin) or other surgical tool (e.g., drill or trocar, to list only a couple of potential tools). As described above, although two pin guides 258 are shown, fewer or more pin guides 258 can be provided. Further, other guide elements can be provided by any one of the body portions 252. For example, one or more cutting guides and/or guide apertures can be provided on any or all of the body portions 252. The gimbal structure of body 252 advantageously enables the pin guides or other guide surfaces or apertures to be adjusted intraoperatively by the surgeon or user in a controlled fashion with respect to a reference point provided by the locating component 102.

Figure 27:
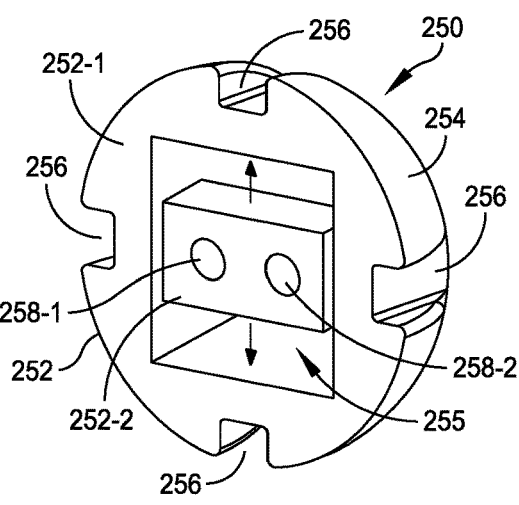
FIG. 27 is a front side isometric view of another example of an adjustable component that can be used with a locating component in accordance with some embodiments.
Figure 28:
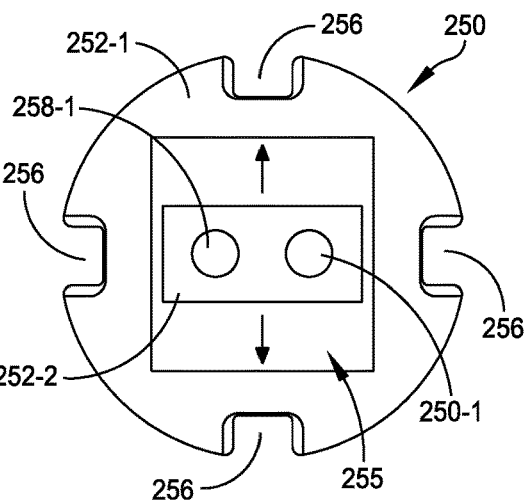
FIG. 28 is a front side view of the adjustable component illustrated in FIG. 27 in accordance with some embodiments.

FIGS. 27 and 28 illustrate another example of a guide insert that permits adjustment of a guide aperture or surface intraoperatively. Guide insert 250 illustrated in FIGS. 27 and 28 includes a first body portion 252-1 and a second body portion 252-2. First body portion 252-1 can have a generally circular shape having a periphery defining one or more channels or grooves 256 for engaging one or more protrusions 122 of a locating component 102. Body portion 252-1 further defines an opening 255 that is sized and configured to receive second body portion 252-2 in a slidable manner. Opening 255 is shown as having a generally rectangular shape, but can have a variety of shapes and sizes. Second body portion 252-2 is shown as having a rectangular shape and defining a pair of guide apertures 258-2, although second body portion 252-2 can be configured to define fewer or more guide apertures and/or different types of guide apertures as discussed herein. It should be understood that fewer or more body portions can be provided, and one or more of the body portions can include guide apertures.

As indicated by the arrows in FIGS. 27 and 28, second body portion 252-2 can be coupled to the first body portion 252-1 such that second body portion 252-2 is configured to move relative to the first body portion 252-1 in at least one direction (e.g., vertically). For example, the coupling between the first and second body portions 252-1, 252-2 can include one or more cooperative mechanical interfaces that permit relative motion between the first and second body portions (e.g., corresponding channels and protrusions, a mortise and tenon, or dovetail connection, to list only a few possibilities).

Figure 29:
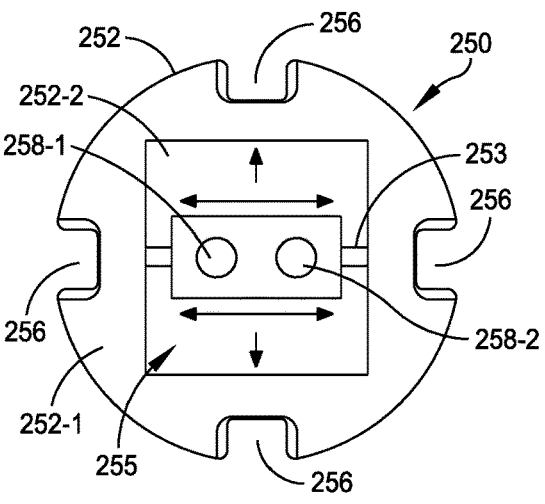
FIG. 29 is a front side view of another example of an adjustable component that can be used with a locating component in accordance with some embodiments.

FIG. 29 illustrates another example of a guide insert in accordance with some embodiments. Guide insert 250 can include a first body portion 252-1 having a generally circular shape that defines one or more channels or grooves 256 along its outer periphery. As described above, the channels or grooves 256 can be configured to receive a protrusion, such as a protrusion 122, of a locating component 102 to coupling and aligning the guide insert 250 to the locating component. Body portion 252-1 can define an opening 255 sized and configured to receive second body portion 252-2.

Second body portion 252-2 can have a rectangular shape and define guide apertures 258. While guide apertures 258 are shown as being round holes sized and configured to receive a fixation element (e.g., k-wire, pin, or the like) and/or other tool (e.g., drill, rotary cutting tool, or the like), one or more of the guide apertures 258 can take other forms (e.g., slots or surfaces). In some embodiments, the second guide body 252-1 can be coupled to one or more pivot bars 253. Pivot bar 253 can allow the second guide body 252-2 to rotate about a longitudinal axis defined by the pivot par 53 and also can allow for the second guide body 252-2 to slide along the axis in a first direction (e.g., horizontally on the page).

In some embodiments, the second guide body 252-2 can be able to move relative to the first guide body 252-1 in a second direction (e.g., vertically on the page) that is different from the first direction. For example, the pivot bar 253 can be able to move within a channel (not show) defined by the first body portion 252-1. One of ordinary skill in the art will understand that other configurations allowing for movement of the second body portion 252-2 relative to the first body portion 252-1 are possible.

Figure 30:
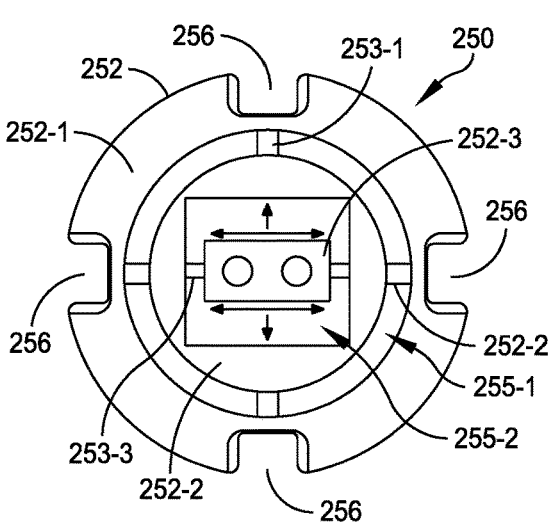
FIG. 30 is a front side view of another example of an adjustable component that can be used with a locating component in accordance with some embodiments.

Turning now to FIG. 30, another example of a guide insert that permits movement relative to a locating component is shown. The guide insert 250 shown in FIG. 30 includes a body 252 having a first body portion 252-1, which can be referred to as an outer body portion, a second body portion 252-2, which can be referred to as a middle body portion, and a third body portion 252-3, which can be referred to as an inner body portion. The first body portion 252-1 is shown as having a circular shape defining one or more grooves or channels 256 along its peripheral surface. In some embodiments, first body portion 252-1 defines a first opening 255-1 sized and configured to receive at least one of the second body portion 255-2 and third body portion 255-3.

Second body portion 252-2 is shown in FIG. 30 as having a circular shape, but second body portion 252-2 can have other shapes or forms. In some embodiments, second body portion 252-2 can be coupled to the first body portion 252-1 via one or more pivot bars, such as pivot bars 253-1, 253-2 shown in FIG. 30. Second body portion 252-2 can define an opening 255-2 that is sized and configured to receive third body portion 252-3.

Third body portion 252-3 is shown in FIG. 30 as having a rectangular shape, but can have other shapes or forms as discussed herein. In some embodiments, third body portion 252-3 can define one or more guide apertures or surfaces 258 for receiving a tool, such as a fixation device or bone removal tool as described above. The third body portion 252-3 can be coupled to one or more pivot bars 253-3, which can be coupled to or supported by second body portion 252-2 such that third body portion 252-3 can move in one or more directions. For example, as indicated by the arrows in FIG. 30, third body portion 252-3 can be able to move in both a first direction (e.g., vertically on the page) and a second direction (e.g., horizontally on the page) relative to at least one of the first and second body portions 252-1, 252-2. In some embodiments, third body portion 252-3 can be configured to rotation about a longitudinal axis defined by pivot bar 253-3.

Figure 31:
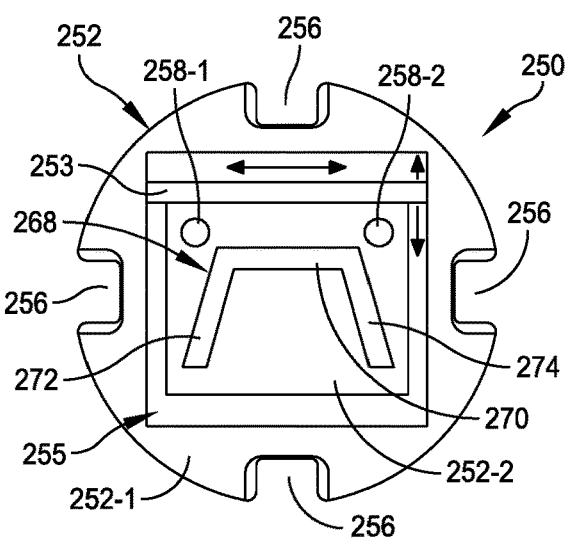
FIG. 31 is a front side view of another example of an adjustable component that can be used with a locating component in accordance with some embodiments.

As noted above, the guide inserts can be provided with various types of guide apertures or surfaces. FIG. 31 illustrates one example of a guide insert 250 having a first body portion 252-1 and a second body portion 252-2, with the second body portion 252-2 being movably coupled to the first body portion 252-1 via a pivot bar 253. The second body portion 252-2 can include a first pin guide 258-1, a second pin guide 258-2, and a cutting guide 268. As shown in FIG. 31, the cutting guide 268 can include a transverse slot 270 and first and second angled slots 272, 274 that extend from opposite ends of transverse slot 270 at oblique angles relative to each other and/or transverse slot 270.

The guide inserts shown in FIGS. 25-31 can be configured to be coupled to a locator component in a single orientation while providing a surgeon or other medical professional or user with the ability to adjust a location and/or orientation of a guide structure intraoperatively. However, it should be understood that the guide inserts illustrated in FIGS. 25-31 can be configured to be adjustable relative to a locating component as described above.

Figure 32:
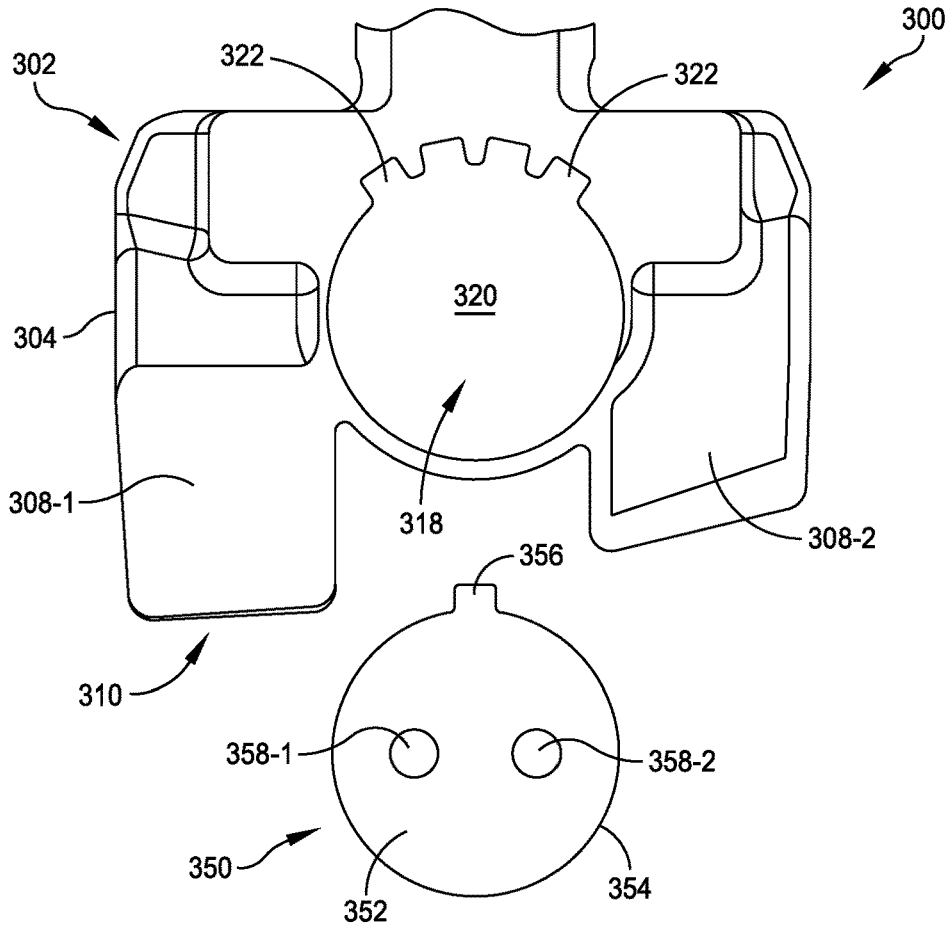
FIG. 32 is a partial front side plan view of another example of a guide including a locating component and an adjustable component in accordance with some embodiments.

FIG. 32 partially illustrates another example of a guide 300 including a locating component 302 and a guide insert 350. The locating component 302 can have a body 304 with a similar shape to that of locating component 102 described above. The coupling element 318 can be located at a more inferior location compared to the location of coupling element 118 described above with respect to FIGS. 1, 2, and 9. For example and as shown in FIG. 32, the coupling element 318 can be located at least partially between legs 308-1, 308-2 (collectively, legs "308") that extend from the inferior end 310 of body 304 such that a portion of the body 304 surrounding and defining the coupling element 318 extends below (e.g., inferiorly) and between legs 308. However, in some embodiments, the body 304 can only partially surround coupling element 318, as will be understood by one of ordinary skill in the art and shown above in FIG. 1.

The guide insert 350 can interface with the body 304 of the locating component 302 such that adjustment of the guide insert relative to the locating component is selectively constrained. For example, the coupling element 318 can define an opening 320 and include one or more notches or recesses 322 in communication with the opening 320. Each recess of the plurality of recesses 322 is sized and configured to receive a protruding detent 356 that extends outwardly from a peripheral edge 354 of the body 352 of the guide insert 350. Although the recesses 322 are shown as being defined by the body 304 of locating component 302 and the detent 356 is shown as extending from the insert guide body 352, it should be understood that the configuration could be reversed such that a detent is located on the locating component body 304 and a plurality of recesses are located along the periphery of the guide insert's body 352. The location of the recesses 322 and/or detent 356 can be predetermined such that a predetermined angular correction can be provided by selecting a recess-protrusion pair for engagement (e.g., in increments of 1°, 2°, 3°, 4°, 5°, etc.). Such angular correction can be selected by a user intraoperatively to correct a varus/valgus alignment of the guide apertures 358 to facilitate a desired change in varus/valgus deformity of the patient. Although not shown in FIG. 32, indicia can be provided adjacent to the notches 322 (or elsewhere along the body 304 of locating component 302) to provide a visual indication of the amount of adjustment provided by the recesses 322. Further, although guide apertures 358 are shown as a pair of holes, it should be understood that the guide insert 350 can be provided with any number of guide apertures and/or surfaces, including those described above with respect to FIGS. 10-20 and 25-31, for example.

Figure 33:
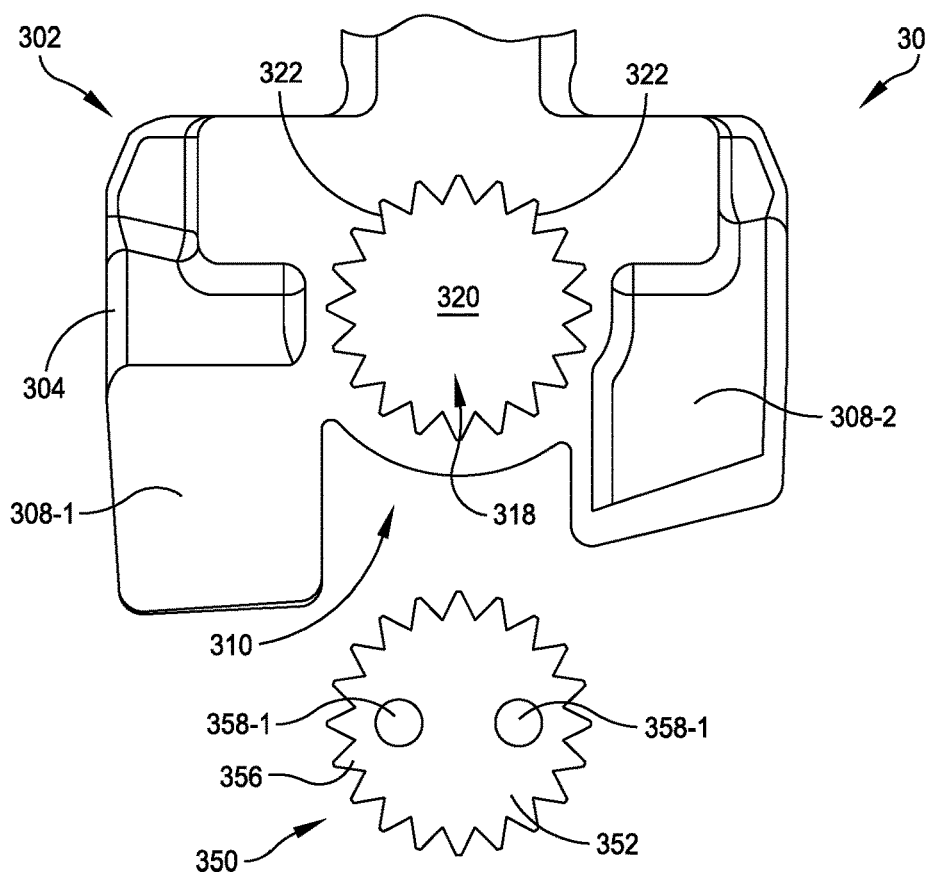
FIG. 33 is a partial front side plan view of another example of a guide including a locating component and an adjustable component in accordance with some embodiments.

FIG. 33 illustrate another example of a guide 300 having a locating component 302 and a guide insert 350, where the guide insert has a gear-shaped interface. More particularly, the example illustrated in FIG. 33 shows locating guide 302 having a coupling element 318 including an opening 320 and a plurality of triangularly shaped recesses 322 encircling the opening, and the body 352 of guide insert 350 including a plurality of detents 356 that have complementary triangular shape. The corresponding recesses 322 and detents 356 can be triangular, as shown, rectangular, or they can have other shapes that are complementary to one another. The detents 356 and recesses 322 can be provided at predetermined intervals that correspond to a specific angular adjustment (e.g., 1°, 2°, 3°, 4°, 5°, etc.) to provide the surgeon or other user with the ability to make a constrained adjustment to the preoperative plan intraoperatively.

Figure 34:
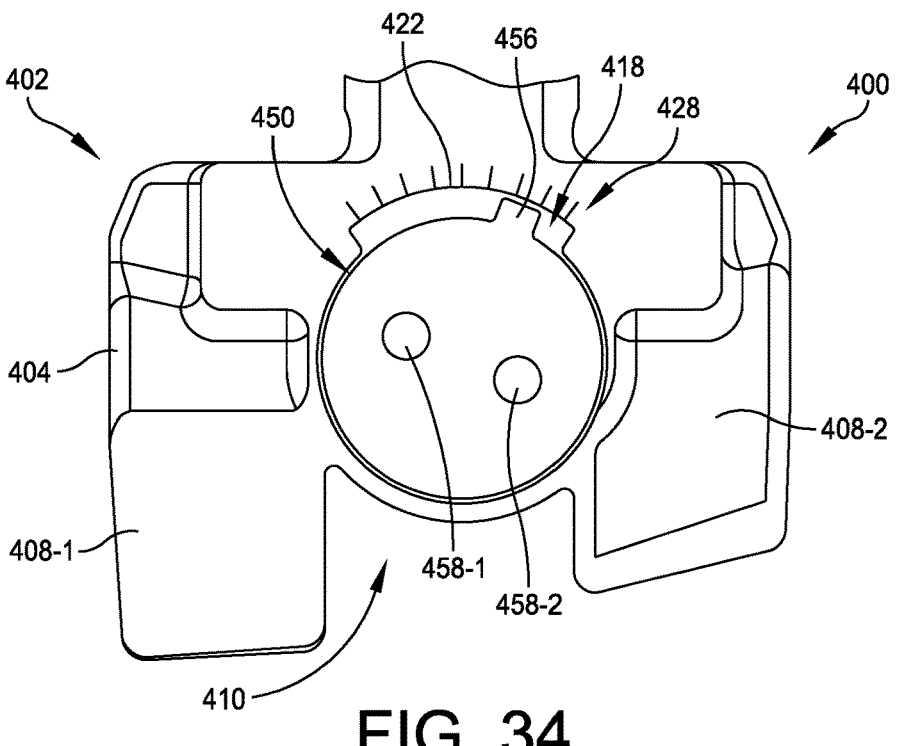
FIG. 34 is a partial front side plan view of another example of a guide including a locating component and an adjustable component in accordance with some embodiments.

FIG. 34 illustrates another example of a guide 400 having a locating component 402 and a guide insert 450 that interface with one another. In the example illustrated in FIG. 34, the interface includes a single protruding detent 456 and a single elongated groove or recess 422. The recess 422 is elongated so that the guide insert 450 can be rotated within an angular range defined by the two ends of the elongated recess 422. The rotation of the guide insert 450 would be around a central axis that is located at the center of the guide insert 450 and oriented orthogonal to the plane of the FIG. 34. One or more markers or indicia 428 can be provided along (e.g., adjacent to) the recess 422. The indicia 428 can provide a visual indication of the angular adjustment when the insert guide 450 is rotated relative to the locating component 402.

Figure 35:
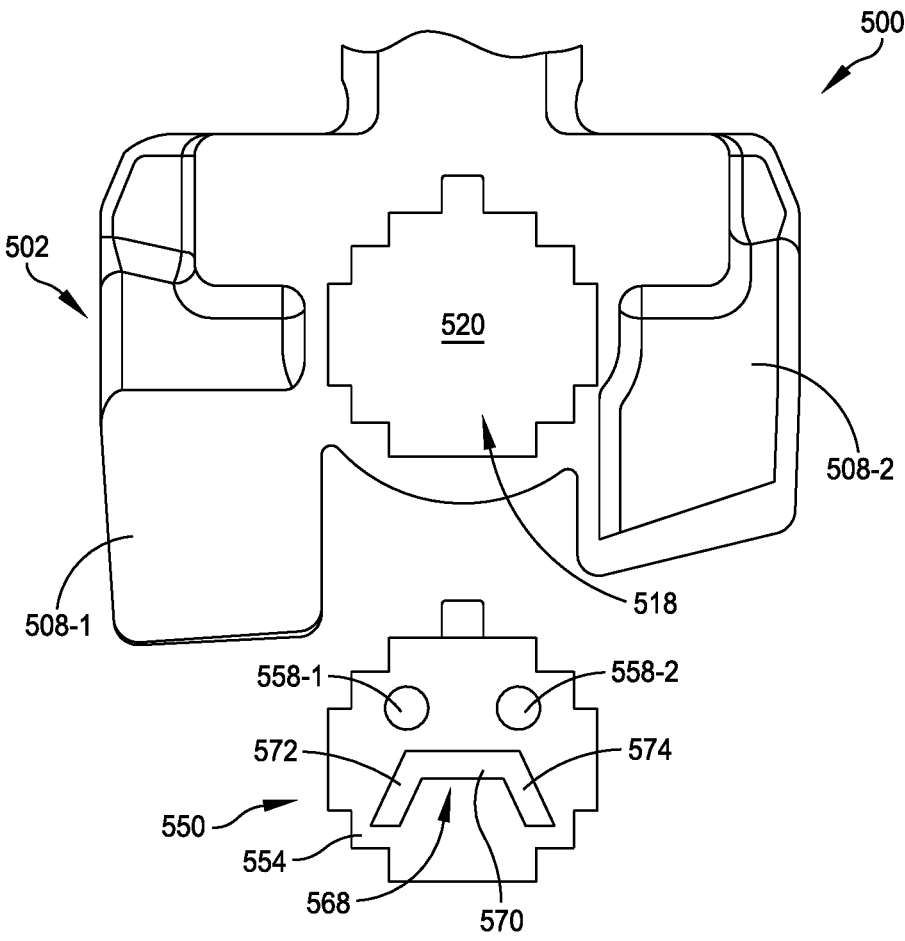
FIG. 35 is a partial front side plan view of another example of a guide including a locating component and an adjustable component in accordance with some embodiments.
Figure 36:
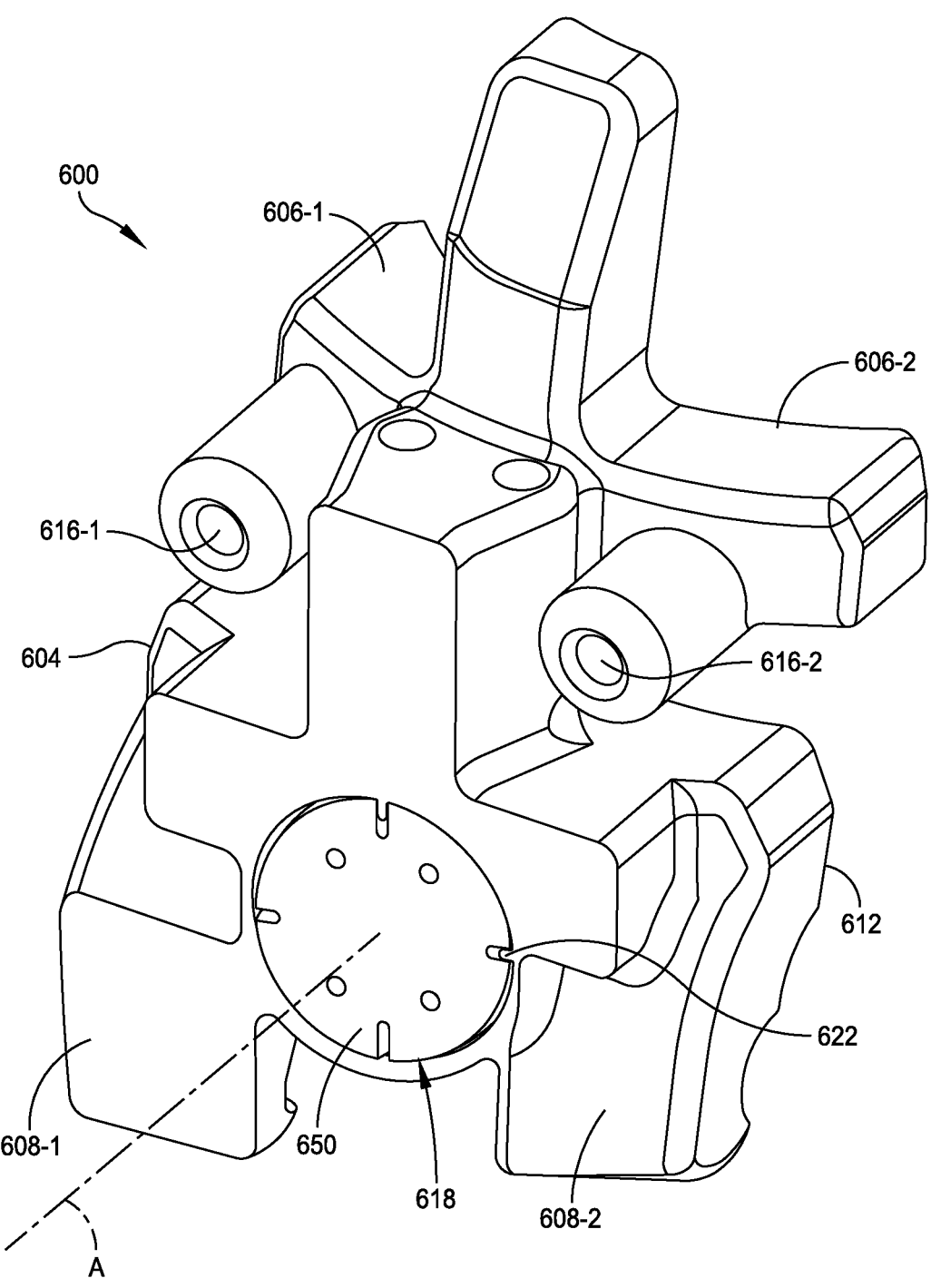
FIG. 36 is a front side isometric view of another example of a guide including a locating component and an adjustable component in accordance with some embodiments.

FIG. 35 illustrates another example of a guide 500 having a locating component 502 and a guide insert 550. In the example illustrated in FIG. 35, the locating component 502 includes a coupling element 518 disposed between first and second legs 508-1, 508-2. The coupling element can include a non-symmetrically shaped opening 520 and a guide insert 550 that has a shape that is complementary to the non-symmetrical shape of the opening 520. This configuration allows the guide insert 550 to be received within the opening 520 in one orientation only. Put another way, the shape of the opening 520 and body 504 of the guide insert 550 are orientationally keyed to one another. The guide insert 550 is shown as including a pair of spaced apart guide apertures 558-1, 558-2 and a cutting guide 568, but it should be understood that the cutting guide can include other features to facilitate the insertion of fixation elements and/or removable of bone as described herein.

FIGS. 36-39 illustrate another example of a patient-specific guide 600. Guide 600 can include a locating component 604, which can support or can be otherwise coupled to an adjustable component 650. In some embodiments, the locating component 604 has a body with a pair of outwardly extending arms 606-1, 606-2 (collectively "arms 606"). A pair of legs 608-1, 608-2 (collectively "legs 608") can extend from the inferior end 610 of the body of the locating component 604. The body of the locating component 604 can further include a first side 612, which can be a bone facing side, and an opposed second side 614. The bone-facing side 612 can include one or more patient specific surfaces that is based on preoperative imaging, as described in U.S. Pat. No. 5,768,134 issued to Swaelens et al., which was incorporated by reference above. In some embodiments, the locating component 604 can be formed from a medical-grade material that is capable of being 3D printed (e.g., additively manufactured), such as ABS, PLA, PETG, nylon, TPU, resin, and other suitable thermoplastics and thermosetting plastics, to list only a few possibilities.

In some embodiments, the body of the locating component 604 defines one or more holes 616-1, 616-2 (collectively, "holes 616"). Holes 616 can be sized and configured to receive a k-wire, pin, or other fixation device for coupling the locating component 604 to one or more bones. In the example illustrated in FIGS. 36 and 37, each arm 606-1, 606-2 defines a respective hole 616-1, 616-2. It should be understood that the body of the locating component 604 can define other holes. For example, each leg 608-1, 608-2 can define a respective hole (not shown) to either increase the securement of locating component 604 to a first bone or to couple the locating component 604 to a second bone (e.g., a talus) while the holes 616 couple the locating component 604 to a first bone (e.g., a tibia). One of ordinary skill in the art will understand that additional holes can be provided and/or holes can be provided at other locations in the body of the locating component 604, such as holes 630-1, 630-2 (collectively, "holes 630"), which can be sized and configured to receive a radiopaque element. For example, one or more radiopaque elements can be received in the one or more holes 630 to provide aid in the alignment of a fluoroscopic device with the guide 600. In some embodiments, the holes 630 are arranged perpendicular with respect to an orientation of holes 616; however, one of ordinary skill in the art will understand that the holes 630 can be arranged parallel to one another and/or holes 616 or can be oriented at other angles.

The body of the locating component 604 can further include a coupling element 618. In the example shown in FIGS. 36 and 37, the coupling element 618 can include an opening 620 defined by the body of the locating component 604 and one or more protrusions 622 that extend inwardly into opening 620 from a peripheral side 624. Although opening 620 is shown as having a circular shape, it should be understood that opening 620 can have other shapes, including those shapes described elsewhere herein. Further, while two protrusions 612 are shown extending inwardly into opening 620, fewer or more protrusions 622 can be provided. Additionally or alternatively, one or more of the protrusions can be omitted or replaced with a channel or groove.

Figure 38:
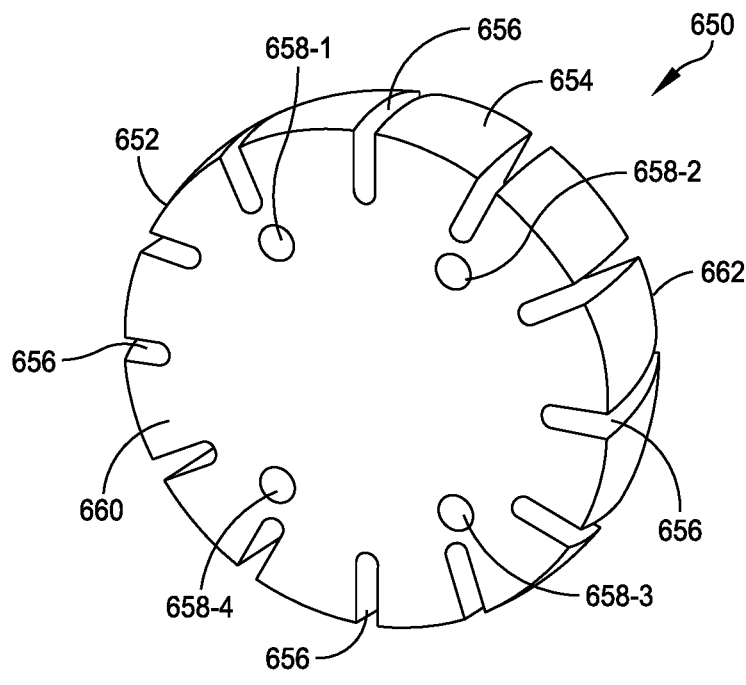
FIG. 38 is a front side isometric view of the adjustable component of the guide illustrated in FIG. 36 in accordance with some embodiments.
Figure 39:
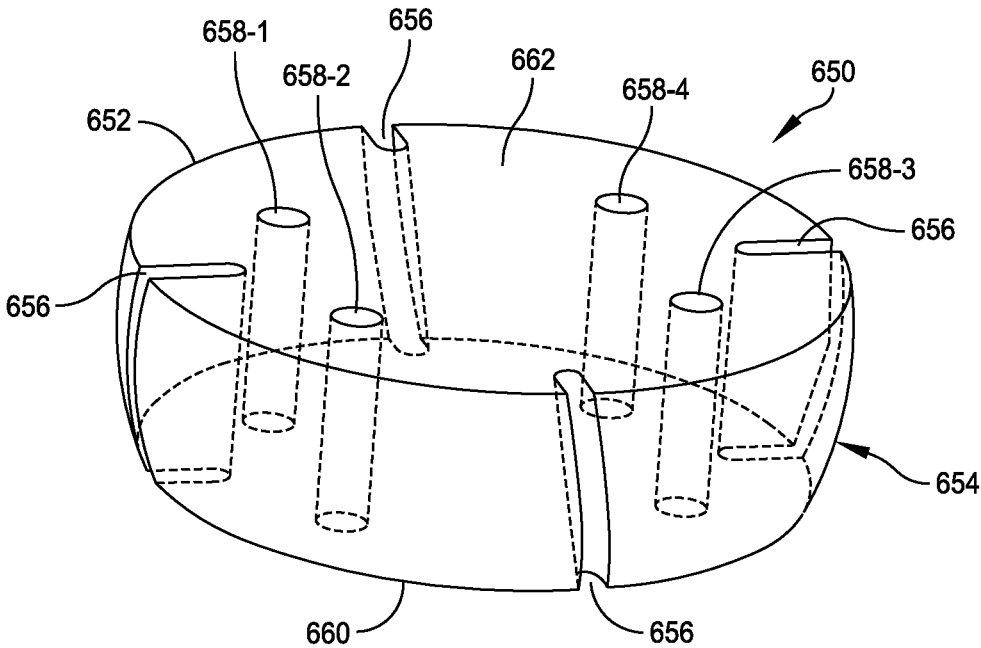
FIG. 39 is a rear side isometric view of the adjustable component of the guide illustrated in FIG. 36 in accordance with some embodiments.

The coupling element 618 can be sized and configured to receive an adjustable component, such as one or more guide inserts 650 in an adjustable manner. The guide insert 650 can include one or more guide apertures or surfaces 658 that can be used to facilitate a surgical process. For example, in the embodiment illustrated in FIGS. 36-39, the body 652 of guide insert 650 is shown as including four pin guides 658-1, 658-2, 658-3, 658-4 (collectively, "pin guides 658"). Pin guides 658 can extend from a first side 660 of body 652 to an opposed second side 662 as best seen in FIGS. 38-39. In the illustrated example, the pin guides 658 are shown as being equidistantly spaced about body 652. However, it should be understood that the number of pin guides 658 can be varied along with the location of the pin guides 658 as described herein.

The guide insert 650 and the coupling element 618 are configured to allow the orientation of the guide insert 650 within the coupling element 618 can be selectively adjusted. For example, guide insert 650 can have a disc-shaped body 652 as best seen in FIGS. 38 and 39. The body 652 of guide insert 650 can be configured to be inserted into the coupling element 618 in certain rotational orientation similar to the embodiment shown in FIG. 33. The rotational orientation refers to the orientation of the guide insert 650 rotated about the central axis A shown in FIGS. 36 and 37.

Figure 37:
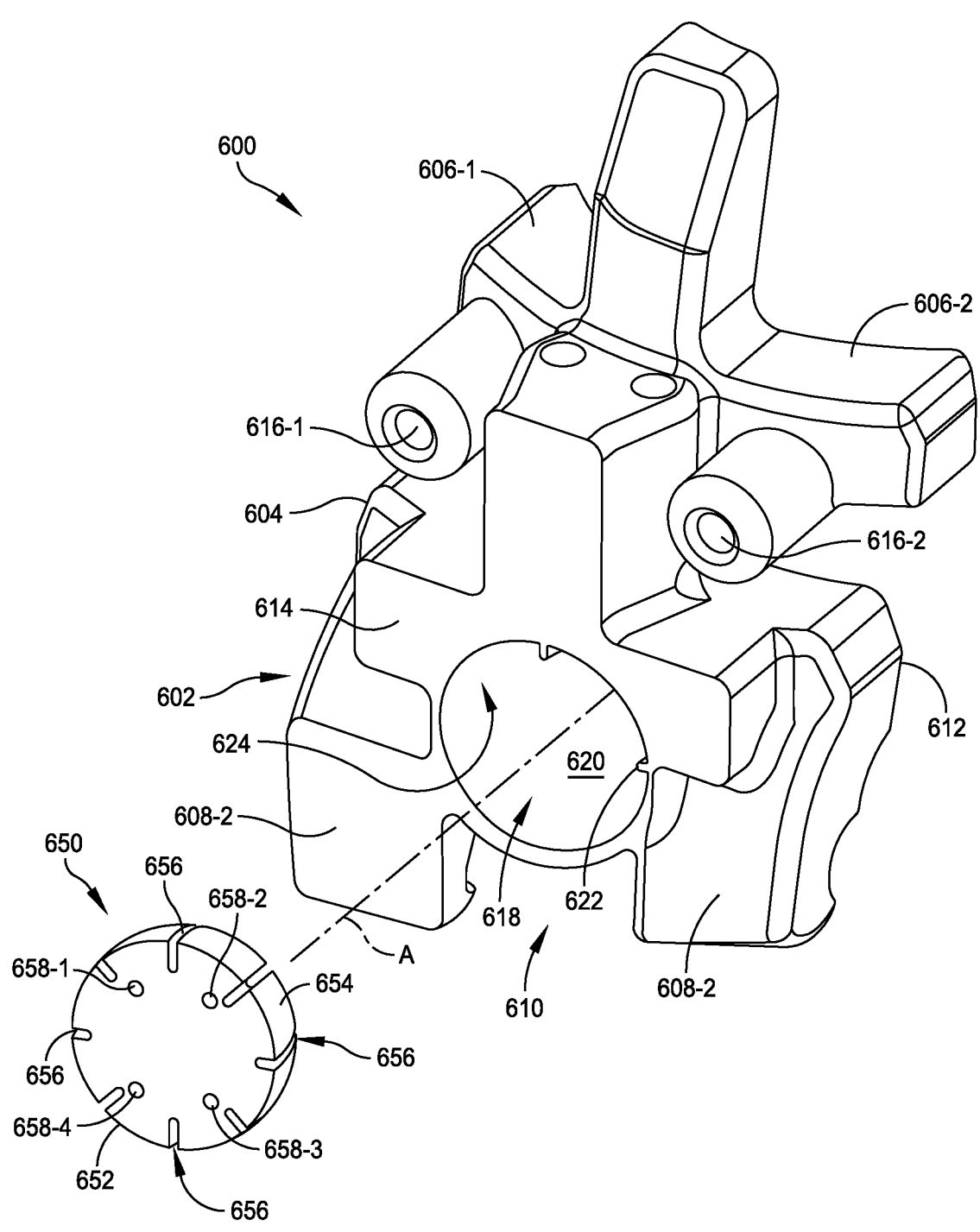
FIG. 37 is an exploded view of the guide illustrated in FIG. 37 in accordance with some embodiments.

Referring to FIG. 37, the guide insert 650 can move in or out of the coupling element 618 in axial direction along the central axis A defined by the opening 620 but once situated within the coupling element 618, the coupling element 618 and the guide insert 650 are configured to prevent the guide insert 650 from rotating about the central axis A relative to the locating component 604. For example, the coupling element 618 can include one or more protruding detents 622 provided along the periphery of the opening 620. The body 652 of guide insert 650 can include complementary slots or grooves 656 that are sized and configured to receive the detents 622. The grooves 656 are spaced apart on the guide insert 650 at predetermined intervals such that the guide insert 650 can be inserted into the opening 620 at various rotational orientation about the central axis A that are rotationally shifted at the predetermined intervals. This allows the operator or surgeon to adjust the orientation of the pin guides 658.

The grooves 656 can be provided on the guide insert 650 at any desired intervals and the number of grooves 656 provided on the guide insert 650 can vary accordingly. For example, the example of the guide insert 650 shown in FIG. 36 has four grooves 656 that are located 90° apart at 12 o'clock, 3 o'clock, 6 o'clock, and 9 o'clock positions and two detents 622 are provided along the periphery of the opening 620 at the corresponding 12 o'clock and 3 o'clock positions. In such embodiment, the guide insert 650 can be inserted into the opening 620 at different rotational orientations at 90° intervals.

In another example of the guide insert 650 shown in FIG. 37, eight grooves 656 are provided on the guide insert 650 located at intervals that are 45° apart. With the two detents 622 provided along the periphery of the opening 620 that are 90° apart, the guide insert 650 can be inserted into the opening 620 at different rotational orientations at 45° intervals.

In yet another example of guide insert 650 shown in FIG. 38, twelve grooves 656 are provided on the guide insert 650 located at intervals that are 30° apart. With the two detents 622 provided along the periphery of the opening 620 that are 90° apart, the guide insert 650 can be inserted into the opening 620 at different rotational orientations at 30° intervals.

In some embodiments, the guide insert 650 can have a side surface 654 that is convex, preferably a spherical surface. The internal surface 624 of the coupling element 618 would be complementary to the spherical contour of the side surface 654 of the guide insert 650. With the embodiments where the side surface 654 has a spherical surface, by configuring the coupling element 618 to have two detents 622 that are positioned at diametrically opposed locations along the periphery of the opening 620, with the guide insert 650 is received and positioned within the opening 620, the guide insert 650 can be rotated about an axis that is orthogonal to the central axis A of the opening 620 and also orthogonal to an imaginary line connecting the two diametrically opposed detents 622. In other words, the detents 622 and grooves 656 provide for a keyed relationship and can prevent the body 652 of the guide insert 650 from moving in a first direction (e.g., rotating about the central axis A) while allowing movement in a second direction (e.g., rotating about an axis that is perpendicular to the central axis defined by the opening 620). The direction of this rotating motion in the second direction in relation to the guide 600 will be predetermined by the locations of the two diametrically opposed detents 622 in a particular version of the guide 600.

The location of the detents 622 along the side 624 and/or the location of the channel or grooves 656 along body 652 can be selected to provide a predetermined amount of adjustment between the guide insert 652 and the locating component 602. However, in some embodiments, the interface between coupling element 618 and the body 652 of guide insert 650 can allow for unconstrained adjustment, which allows guide insert 650 to be rotated in a complete circle within coupling element 118 as described herein. The body 652 of guide insert 150 can be able to fit only partially within coupling element 618, or body 652 can be configured such that the entirety of the body 652 can be received within the coupling element 618 as shown in FIG. 37.

The body 652 of guide insertion 650 can have a shape other than a circular disk. For example, the body 652 can be shaped as a rectangular or square, triangular, cruciform, or gear shaped, to list one a few possibilities. It should be understood that the coupling element 618 can have a complementary shape to the body 652 of the guide insert such that the guide insert 650 can be coupled to the locating component 602. In some embodiments, the guide insert can be configured to be moved (e.g., rotated, pivoted, and/or repositioned) relative to the locating component. However, in some embodiments, as described below, the guide insert 650 can be coupled to locating component in a single orientation, but permit guide apertures and surfaces to be repositioned.

As described above, the pin guides 658 can be arranged parallel to one another and disposed perpendicular with respect to a plane defined by one or more of the faces of the body 652. However, the pin guides 658 can also be disposed in a non-parallel arrangement with one another and at an oblique angle with respect to a plane defined by the one or more faces of the body 652. Further, pin guides can be provided with a bushing (not shown). The pin guides 658 can be sized and configured to receive a pin, k-wire, or other fixation element, as will be understood by one of ordinary skill in the art. Additionally or alternatively, the opening of the pin guides 658 can be sized and configured to receive a bone removal tool, such as a drill bit or rotary cutting tool. In some embodiments, the body 652 of the guide insert 650 can be formed from a material that is more rigid and/or durable than the material from which the locating component is formed. For example, the guide insert body 652 can be formed from a medical-grade metal, such as titanium, stainless steel, cobalt, and/or chromium, to list only a few possible materials. Further, the guide insert body 652 can be machined and/or formed using an additive manufacturing process, such as EBM or DMLS, to list only a couple possibilities.

Advantageously, the coupling between locating component 602 and guide insert 650 allows a surgeon or other user to adjust a location at which a fixation element and/or bone removal tool is applied to bone. As noted above, the user can make the decision to adjust a relative position between the guide insert 650 and locating component 602 intraoperatively in response to viewing the surgical site.

In use, a locating component 102, 302, 402, 502, 602 can be placed relative to a first bone such that at least one patient-specific surface of the locating component is coupled to at least one bone. As will be understood by one of ordinary skill in the, the at least one patient-specific surface can engage a predetermined area of a first tissue (e.g., bone or cartilage) in a predetermined way based on preoperative imaging and analysis. One or more fixation elements, such as a k-wire or pin, can be inserted into the locating element to secure the locating element to a first tissue (e.g., bone or cartilage).

In some embodiments, the locating component 102, 302, 402, 502, 602 can be configured to engage more than one bone. For example, the locating component 102, 302, 402, 502, 602 can include a first patient-specific surface configured to engage a first bone and a second patient-specific surface configured to engage a second bone. In such embodiments, the locating component 102, 302, 402, 502, 602 can be placed such that the first patient-specific surface engages the first bone and the second patient-specific surface engages the second bone. It should be understood that the locating component can include additional patient-specific surfaces, which can be configured to engage the first bone, the second bone, and/or a third bone.

An adjustable component 150, 250, 350, 450, 550, 650 can be coupled to the locating component 102, 302, 402, 502, 602 prior to and/or after the locating component 102, 302, 402, 502, 602 is coupled to the one or more bones. As described above, the adjustable component 150, 250, 350, 450, 550, 650 can be coupled to the locating component 102, 302, 402, 502, 602 via a coupling element.

With an adjustable component 150, 250, 350, 450, 550, 650 coupled to locating component 102, 302, 402, 502, 602 and the locating component positioned against one or more bones, a surgeon or other medical professional or user can adjust a position of a guide aperture or surface intraoperatively. For example, the adjustable component 150, 250, 350, 450, 550, 650 can be pivoted and/or rotated relative to the locating component 102, 302, 402, 502, 602 to adjust a location of at least one guide aperture or surface of the adjustable component. The adjustment can be made by the surgeon or medical professional in response to conditions present in the operating theater, which can not have been identified during the preoperative planning stages. For example, bone quality and/or one or more deformities can have changed since the preoperative planning stage or during the surgical intervention, and the surgeon or medical professional would like to make an adjustment based on the conditions identified intraoperatively. Accordingly, the adjustable component can be used to provide the desired adjustment, such as by rotating or otherwise moving the adjustable component relative to the locating component.

As described above, there can be one or more ways in which an adjustable component 150, 250, 350, 450, 550, 650 can be moved to provide the adjustment of a guide surface or aperture relative to the locating component 102, 302, 402, 502, 602. For example, in some embodiments, a first adjustable component can be removed from its engagement with the locating component and replaced with a second locating component, which can be selected from a plurality of available adjustable components.

In some embodiments, the adjustable component 150, 250, 350, 450, 550, 650 can be pivoted, rotated, and/or moved linearly in one or more directions, such as by sliding, relative to the locating component 102, 302, 402, 502, 602. For example, the entire locating component and/or a portion of a locating component can be moved relative to the locating component as described herein.

Once the desired adjustment has been made, the adjustable component 150, 250, 350, 450, 550, 650 can be used to guide another surgical tool. For example, one or more holes defined by the adjustable component 150, 250, 350, 450, 550, 650 can be used to guide the placement of a fixation element or device (e.g., a k-wire or pin) into one or more bones. Additionally or alternatively, one or more guide surfaces or slots of the adjustable component 150, 250, 350, 450, 550, 650 can be used to guide a cutting instrument (e.g., a saw or drill) to remove tissue (e.g., bone, cartilage, etc.) from the patient in a controlled manner. As noted above, the locating component can be left in position on the one or more bones while the fixation element and/or cutting instrument is used, or the locating component can be removed from its engagement with the one or more bones while the fixation element and/or cutting instrument is used.

The systems, guides, and kits described herein advantageously enable a surgeon or other medical professional to make an intraoperative adjustment to a location of a guide aperture or surface that is placed relative to a tissue using a patient-specific locating guide. The intraoperative adjustability of the guide aperture or surface advantageously enables a surgeon to adjust a preoperative plan to address issues identified in the operating theatre.

Although the systems, guides, kits, and methods have been described in terms of exemplary embodiments, they are not limited thereto. Rather, the appended claims should be construed broadly, to include other variants and embodiments of the systems, guides, kits, and methods, which can be made by those skilled in the art without departing from the scope and range of equivalents.

What is claimed is:

1. A system, comprising:
a first component having a first body, the body having a first side and an opposed second side, the first side having at least one patient-specific surface configured to engage at least one bone in a predetermined manner, the first body having a coupling element; and
a second component having a second body, the second body sized and configured to engage the coupling element to couple the second component to the first component, the second body including at least one guide surface that defines at least one hole sized and configured to receive a fixation device with a first slot and a second slot each configured to receive a cutting instrument, the first slot configured to guide the cutting instrument for resecting a first bone and the second slot configured to guide the cutting instrument for resecting a second bone that is different from the first bone wherein the at least one hole extends through the second body along an axis that is disposed at an oblique angle with respect to a plane defined by a first side of the second body and is at least partially defined by a bushing that extends from the second body, wherein a position of the at least one guide surface is configured to be adjusted relative to the first component intraoperatively.

2. The system of claim 1, wherein the coupling element includes an opening defined by the first body of the first component, and wherein the second body is sized and configured to be at least partially received within the opening.

3. The system of claim 2, wherein the second body is configured to rotate freely within the opening about an axis defined by the opening.

4. The system of claim 3, wherein the first body includes indicia adjacent to the opening.

5. The system of claim 2, wherein the second body is configured to be rotated selectively within the opening about an axis defined by the opening.

6. The system of claim 5, wherein the second body defines at least one groove, the first body includes at least one protrusion, and the at least one protrusion is sized and configured to be received in the at least one groove; or wherein the second body includes at least one protrusion, the first body defines at least one groove, and the at least one protrusion is sized and configured to be received in the at least one groove.

7. The system of claim 6, wherein the second body is configured to pivot about an axis that is oriented at an angle relative to the axis defined by the opening.

8. The system of claim 1, wherein the second body includes a first body portion and a second body portion, and wherein the second body portion defines the at least one guide surface and is configured to move relative to the first body portion.

9. The system of claim 8, wherein the second body portion is coupled to the first body portion by at least one pivot bar; or wherein the second body portion is configured to move in first and second directions relative to the first body portion.

10. The system of claim 9, wherein the first and second directions are orthogonal relative to one another.

11. The system of claim 1, wherein the second body includes a first body portion, a second body portion, and a third body portion, and wherein the first body portion, second body portion, and third body portion collectively form a gimbal.

12. The system of claim 1, wherein the first body includes:

a first patient-specific surface configured to engage a first bone, and a second patient-specific surface configured to engage a second bone.

13. The system of claim 12, wherein the second component defines a first guide surface and a second guide surface, the first guide surface is configured to be disposed adjacent to the first bone when the second component is coupled to the first component and the first patient-specific surface engages the first bone, and the second guide surface is configured to be disposed adjacent to the second bone when the second component is coupled to the first component and the second patient-specific surface engages the second bone.

\* \* \* \* \*